(12) United States Patent
Matsumoto et al.

(10) Patent No.: US 11,560,540 B2
(45) Date of Patent: Jan. 24, 2023

(54) CELL TREATMENT APPARATUS AND METHOD FOR TREATING CELLS WITH LASERS

(71) Applicant: KATAOKA CORPORATION, Kyoto (JP)

(72) Inventors: Junichi Matsumoto, Kyoto (JP); Shoichi Honda, Kyoto (JP)

(73) Assignee: Kataoka Corporation, Kyoto (JP)

( * ) Notice: Subject to any disclaimer, the term of this patent is extended or adjusted under 35 U.S.C. 154(b) by 468 days.

(21) Appl. No.: 16/627,154

(22) PCT Filed: May 30, 2019

(86) PCT No.: PCT/JP2019/021607
§ 371 (c)(1),
(2) Date: Dec. 27, 2019

(87) PCT Pub. No.: WO2020/003883
PCT Pub. Date: Jan. 2, 2020

(65) Prior Publication Data
US 2021/0071128 A1 Mar. 11, 2021

(30) Foreign Application Priority Data
Jun. 29, 2018 (JP) .............................. JP2018-124805

(51) Int. Cl.
*C12M 3/00* (2006.01)
*C12M 1/00* (2006.01)
*C12M 1/36* (2006.01)

(52) U.S. Cl.
CPC ............ *C12M 39/00* (2013.01); *C12M 31/04* (2013.01); *C12M 41/48* (2013.01)

(58) Field of Classification Search
CPC .............................. C12M 31/04; C12M 41/48
See application file for complete search history.

(56) References Cited

U.S. PATENT DOCUMENTS

| 4,301,252 A | 11/1981 | Baker et al. |
| 5,792,427 A | 8/1998 | Hugh et al. |

(Continued)

FOREIGN PATENT DOCUMENTS

| CN | 1154475 | 7/1997 |
| CN | 1251528 | 4/2000 |

(Continued)

OTHER PUBLICATIONS

Extended European Search Report issued in European Patent Application No. 17896294.0, dated Oct. 22, 2020, 8 pages.

(Continued)

*Primary Examiner* — Nathan A Bowers
(74) *Attorney, Agent, or Firm* — Hamre, Schumann, Mueller & Larson, P.C.

(57) ABSTRACT

The present invention is intended to provide a cell treatment apparatus and a method for treating cells that can suppress a variation of a treatment time of treating cells using laser light. The cell treatment apparatus of the present invention includes: a cell treatment chamber in which cells in a cell culture vessel are treated; an observation unit that can observe the cells; a laser projection unit that can project a laser image onto the cells; a laser moving unit that can move the laser projection unit; and a control unit. The laser projection unit includes: a laser light source; and a laser image generation portion that generates the laser image to be projected onto the cells from laser light oscillated from the laser light source. The control unit controls generation of the laser image by the laser image generation portion. By moving the laser moving unit from a projection start position of the laser image at one end of the cell culture vessel to a projection end position of the laser image at the other end of the cell culture vessel, the laser projection unit projects the laser image from the projection start position of the laser (Continued)

image at one end of the cell culture vessel to the projection end position of the laser image at the other end of the cell culture vessel.

12 Claims, 16 Drawing Sheets

(56) References Cited

U.S. PATENT DOCUMENTS

| | | | |
|---|---|---|---|
| 5,874,266 | A | 2/1999 | Palsson |
| 6,033,396 | A | 3/2000 | Huang et al. |
| 6,143,535 | A | 11/2000 | Palsson |
| 6,281,670 | B1 | 8/2001 | Sugihara et al. |
| 6,699,238 | B1 | 3/2004 | Sagehashi et al. |
| 2001/0005586 | A1 | 6/2001 | Palsson et al. |
| 2002/0076744 | A1 | 6/2002 | Koller et al. |
| 2002/0177885 | A1 | 11/2002 | Eisfeld et al. |
| 2003/0031602 | A1 | 2/2003 | Weselak et al. |
| 2003/0148393 | A1 | 8/2003 | Woodbury |
| 2004/0043392 | A1 | 3/2004 | Washiyama et al. |
| 2004/0063195 | A1 | 4/2004 | Tamaoki et al. |
| 2005/0095578 | A1 | 5/2005 | Koller et al. |
| 2005/0202558 | A1 | 9/2005 | Koller et al. |
| 2005/0276456 | A1 | 12/2005 | Yamato et al. |
| 2007/0160280 | A1 | 7/2007 | Schutze et al. |
| 2008/0057558 | A1 | 3/2008 | Niwa et al. |
| 2010/0328434 | A1 | 12/2010 | Kiyota |
| 2013/0023025 | A1 | 1/2013 | Sumaru et al. |
| 2013/0045187 | A1 | 2/2013 | Semechkin et al. |
| 2013/0327195 | A1 | 12/2013 | Routamaa et al. |
| 2014/0099695 | A1 | 4/2014 | Furuta et al. |
| 2015/0044770 | A1 | 2/2015 | Kim |
| 2018/0142193 | A1 | 5/2018 | Suzuki et al. |
| 2018/0354076 | A1 | 12/2018 | Suzuki et al. |
| 2018/0356321 | A1* | 12/2018 | Sase .................. G01N 1/30 |
| 2020/0325432 | A1 | 10/2020 | Matsumoto |

FOREIGN PATENT DOCUMENTS

| | | |
|---|---|---|
| CN | 103354896 | 10/2013 |
| CN | 103502425 | 1/2014 |
| CN | 203663257 U | 6/2014 |
| EP | 1 784 633 | 5/2007 |
| EP | 3 467 091 | 4/2019 |
| JP | 4-356183 | 12/1992 |
| JP | 2002-511843 | 4/2002 |
| JP | 2003-284549 | 10/2003 |
| JP | 2004-113153 | 4/2004 |
| JP | 2004-350641 | 12/2004 |
| JP | 2005-333889 | 12/2005 |
| JP | 2007-514407 | 6/2007 |
| JP | 2009-082144 | 4/2009 |
| JP | 2009-195110 | 9/2009 |
| JP | 2010-154793 | 7/2010 |
| JP | 4512206 B | 7/2010 |
| JP | 4728319 B | 7/2011 |
| JP | 2011-206066 | 10/2011 |
| JP | 2012-130341 | 7/2012 |
| JP | 5087192 B | 11/2012 |
| JP | 2014-064518 | 4/2014 |
| JP | 2014-509192 | 4/2014 |
| JP | 5580755 B | 8/2014 |
| JP | 6033980 B | 11/2016 |
| JP | 2017-012027 | 1/2017 |
| WO | 2004/037968 | 5/2004 |
| WO | 2006/024819 | 3/2006 |
| WO | 2006/088154 | 8/2006 |
| WO | 2011/125615 | 10/2011 |
| WO | 2016/194454 | 12/2016 |
| WO | 2017/002422 | 1/2017 |
| WO | WO-2017-002422 A1 * | 1/2017 |
| WO | 2017/208589 | 12/2017 |
| WO | 2018/047702 | 3/2018 |

OTHER PUBLICATIONS

Office Action issued in U.S. Appl. No. 15/576,228, dated Oct. 7, 2019, 11 pages.
Hohenstein Elliott, K. A., et al., "Laser-Based Propagation of Human iPS and ES Cells Generates Reproducible Cultures with Enhanced Differentiation Potential", Stem Cells international, 2012, vol. 2012, Article ID: 926463, pp. 1-13.
Office Action of the corresponding Japanese Patent Application (No. 2017-024511) dated Jan. 22, 2019, 12 pages with translation.
Office Action of the corresponding Japanese Patent Application (No. 2017-024512) dated Jan. 22, 2019, 11 pages with translation.
International Search Report and Written Opinion issue in PCT/JP2019/021607, dated Aug. 20, 2019, 13 pages.
Extended European Search Report in the corresponding European Patent Application No. 19826059.8, dated Mar. 4, 2022, 7 pages.
Office Action issued in co-pending U.S. Appl. No. 16/485,356 dated Dec. 22, 2021, 19 pages.
U.S. Appl. No. 16/485,356, filed Aug. 12, 2019.
U.S. Appl. No. 16/485,367, filed Aug. 12, 2019.
Office Action issued in co-pending U.S. Appl. No. 16/485,367, dated Oct. 4, 2021, 39 pages.

* cited by examiner

CELL TREATMENT APPARATUS AND METHOD FOR TREATING CELLS WITH LASERS

TECHNICAL FIELD

The present invention relates to a cell treatment apparatus and a method for treating cells with lasers.

BACKGROUND ART

In recent years, attempts have been made to differentiate target cells, tissues, and the like from pluripotent cells such as induced pluripotent stem cells (iPS cells) and embryonic stem cells (ES cells) and to utilize them for regenerative medicine and drug discovery.

In maintaining the pluripotent cells, some of the proliferating pluripotent cells may differentiate into other cells. In addition, in differentiation from pluripotent cells to target cells or the like, some of differentiated cells may differentiate into cells that are not the target cells.

In such a case, the removal of cells other than the target cells is currently performed manually. However, this removing operation requires time and labor, for example, to be performed under a microscope, and there is a problem that the quality of cells and the like obtained differs greatly depending on the skill level of the operator (Patent Literature 1).

CITATION LIST

Patent Literature

Patent Literature 1: JP 2014-509192 A

SUMMARY OF INVENTION

Technical Problem

Regarding the above-mentioned problem, the inventors of the present invention have attempted, by irradiating the target cells with laser light, to directly or indirectly kill, liberate, and the like to remove the cells. However, the laser light makes an image as a point on the cells. For this reason, a problem has arisen in that the treatment time by the laser light varies greatly in accordance with the area occupied by the target cells in the cell culture vessel.

With the foregoing in mind, it is an object of the present invention to provide a cell treatment apparatus and a method for treating cells that can suppress a variation of a treatment time of treating cells using laser light.

Solution to Problem

In order to achieve the above object, the present invention provides a cell treatment apparatus including: a cell treatment chamber in which cells in a cell culture vessel are treated; an observation unit that can observe the cells; a laser projection unit that can project a laser image onto the cells; a laser moving unit that can move the laser projection unit; and a control unit, wherein the laser projection unit includes: a laser light source; and a laser image generation portion that generates the laser image to be projected onto the cells from laser light oscillated from the laser light source, the control unit controls generation of the laser image by the laser image generation portion, and by moving the laser moving unit from a projection start position of the laser image at one end of the cell culture vessel to a projection end position of the laser image at the other end of the cell culture vessel, the laser projection unit projects the laser image from the projection start position of the laser image at one end of the cell culture vessel to the projection end position of the laser image at the other end of the cell culture vessel.

The present invention also provides a method for treating cells with lasers (hereinafter also referred to as "treatment method"), the method including: a treatment step of performing laser treatment by projecting a laser image onto cells in a cell culture vessel, wherein in the treatment step, the laser treatment is performed by projecting the laser image from a projection start position of the laser image at one end of the cell culture vessel to a projection end position of the laser image at the other end of the cell culture vessel.

Advantageous Effects of Invention

According to the cell treatment apparatus and the treatment method of the present invention, it is possible to suppress a variation of a treatment time of treating cells using laser light.

DESCRIPTION OF EMBODIMENTS

Figure 1:
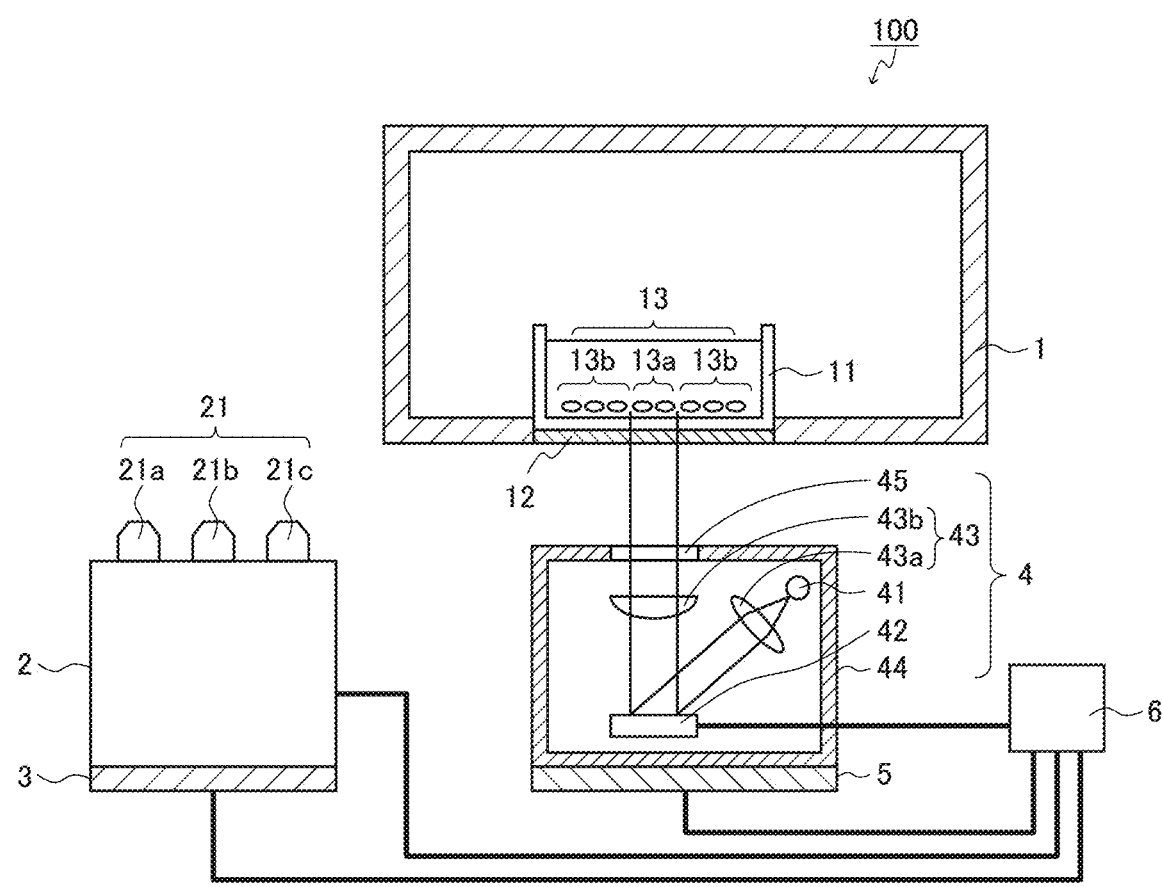
FIG. 1 is a schematic view showing an example of a cell treatment apparatus according to the first embodiment.

In the following description of the present invention, the "Z-axis direction" refers to a direction perpendicular to the plane direction of the bottom surface of the cell culture vessel when the cell culture vessel is placed in the cell treatment chamber, the "X-axis direction" refers to one direction in the plane (XY plane) direction of the bottom surface of the cell culture vessel, and the "Y-axis direction" refers to a direction orthogonal to the X-axis direction in the plane direction of the bottom surface of the cell culture vessel.

In the present invention, "treatment of cells" refers to treatment of cells such as cell killing, removal of unwanted cells by liberation or the like from a cell culture vessel, selection of wanted cells, and shape-processing or the like of aggregates of cells such as a cell sheet, an organ, and the like.

The cell treatment apparatus and the treatment method of the present invention is described in detail below with reference to the drawings. It is to be noted, however, that the present invention is by no means limited or restricted by the following description. Note that the same reference signs may be given to the same components in FIGS. 1 to 16 below and descriptions thereof may be omitted. Furthermore, for convenience in explanation, the structure of each component shown in the drawings may be appropriately simplified, and the size, the ratio, and the like of components may be schematically shown and may be different from actual ones. Regarding the descriptions of the embodiments, reference can be made to each other unless otherwise stated.

First Embodiment

The present embodiment relates to an example of a cell treatment apparatus. FIG. 1 is a schematic cross-sectional view showing a configuration of a cell treatment apparatus 100 according to the first embodiment. As shown in FIG. 1, the cell treatment apparatus 100 includes a cell treatment chamber 1, an observation unit 2, an observation moving unit 3, a laser projection unit 4, a laser moving unit 5, and a control unit 6 as main components. The cell treatment chamber 1 includes a cell culture vessel placement portion 12 in which the cell culture vessel 11 is placed. The cell culture vessel placement portion 12 is formed as a recess on the bottom surface (the laser projection unit 4 side in FIG. 1) of the cell treatment chamber 1. The bottom surface of the cell culture vessel placement portion 12 is formed of a translucent member that can transmit laser light. The cell culture vessel 11 contains cells 13 and is placed in the cell culture vessel placement portion 12. The cells 13 include cells 13a to be treated (hereinafter, may also referred to as "target cells 13a") and cells 13b not to be treated (hereinafter, may also referred to as "non-target cells 13b"). The observation unit 2 includes three objective lenses 21a, 21b, and 21c. The laser projection unit 4 includes a laser light source 41, a laser image generation portion 42, a projection optical system 43, and a housing 44. The laser light source 41, the laser image generation portion 42, and the projection optical system 43 are accommodated in the housing 44. The housing 44 has an opening 45 at the upper part (the cell treatment chamber 1 side in FIG. 1). The projection optical system 43 includes lenses 43a and 43b. The control unit 6 is connected to the observation unit 2, the observation moving unit 3, the laser image generation portion 42, and the laser moving unit 5. While the cell treatment apparatus 100 includes the cell culture vessel 11 containing the cells 13, the cell culture vessel placement portion 12, the observation moving unit 3, the projection optical system 43, the housing 44, and the laser moving unit 5, these members are optional and the cell treatment apparatus 100 may or may not include them.

The cell treatment chamber 1 is a chamber in which cells are treated. The cell treatment chamber 1 may be, for example, a box-shaped housing or the like. In the cell treatment chamber 1, for example, the cell culture vessel 11 containing the cells 13 therein can be placed. As described below, the cells 13 in the cell culture vessel 11 are treated by, for example, laser images projected from the laser projection unit 4. Thus, the region in the cell treatment chamber 1 where the cell culture vessel 11 is to be placed is configured such that, for example, laser images generated by the laser projection unit 4 can be projected onto the cells 13 in the cell culture vessel 11. As a specific example, when the cell culture vessel 11 is placed in the cell treatment chamber 1 and the laser projection unit 4 is placed outside the cell treatment chamber 1, it is preferable that the region in the cell treatment chamber 1 where the cell culture vessel 11 is to be placed be configured such that the laser images projected from the laser projection unit 4 can be transmitted from the outside to the inside of the cell treatment chamber 1. When the cell treatment chamber 1 includes the cell culture vessel placement portion 12 as in the cell treatment apparatus 100 according to the present embodiment, the bottom surface of the cell culture vessel placement portion 12 is made of, for example, a translucent member. The "translucent member" refers to, for example, a member that can transmit laser light such as the laser image or the like, and specific examples thereof include a transparent glass plate and an acrylic plate. While the cell culture vessel placement portion 12 is formed as a part of the cell treatment chamber 1 in the present embodiment, the cell culture vessel placement portion 12 may be formed as a separate member from the cell treatment chamber 1. The cell culture vessel placement portion 12 may be, for example, a stage or the like in a microscope or the like. The gas transfer between inside and outside of the cell treatment chamber 1 is preferably regulated. This can prevent, for example, gas outside the cell treatment apparatus 100 and dust contained in the gas from flowing into the cell treatment chamber 1. While the cell culture vessel 11 containing the cells 13 therein is placed in the cell culture vessel placement portion 12 in the cell treatment chamber 1 in the cell treatment apparatus 100 of the present embodiment, the cell culture vessel 11, the cell culture vessel placement portion 12, and the cells 13 are optional, and the cell treatment apparatus 100 may or may not include them. Furthermore, while the cell treatment apparatus 100 according to the present embodiment includes the cell treatment chamber 1, the cell treatment apparatus 100 may not include the cell treatment chamber 1.

The cell treatment chamber 1 may further include, for example, a temperature regulating unit for regulating the temperature of the cell culture vessel 11. By providing the temperature regulating unit, the culture condition during the treatment of the cells 13 in the cell culture vessel 11 can be kept constant, and for example, damage to the cells 13 can be reduced at the time of imaging the cells 13 and at the time of projecting the laser image to be described below. The temperature regulating unit may be, for example, a heating unit such as a heater or the like. When the cell treatment chamber 1 includes the cell culture vessel placement portion 12, the cell culture vessel placement portion 12 includes, for example, the temperature regulating unit.

The cell treatment chamber 1 may further include, for example, a pH regulating unit for regulating the pH of the culture medium in the cell culture vessel 11. By providing the pH regulating unit, the culture condition during the treatment of the cells 13 in the cell culture vessel 11 can be kept constant, and, for example, damage to the cells 13 can be reduced at the time of imaging the cells 13 and at the time of projecting the laser image to be described below. The pH regulating unit may be, for example, a carbon dioxide concentration regulating unit, and as a specific example, the pH regulating unit may a connecting portion connected to a carbon dioxide supply unit provided outside the cell treatment apparatus 100. When the cell treatment chamber 1 includes the cell culture vessel placement portion 12, the cell culture vessel placement portion 12 includes, for example, the pH regulating unit.

The cell culture vessel 11 is not particularly limited, and may be, for example, a culture vessel such as a known dish, a flask, or the like used for cell culture. The material for forming the cell culture vessel 11 is not particularly limited, and may be, for example, a material that transmits the laser image projected by the laser projection unit to be described below, and specific examples thereof include plastics and glasses that transmit lasers. Examples of the plastic include polystyrene polymers, acrylic polymers (polymethyl methacrylate (PMMA) and the like), polyvinylpyridine polymers (poly(4-vinylpyridine), 4-vinylpyridine-styrene copolymers and the like), silicone polymers (polydimethylsiloxane and the like), polyolefin polymers (polyethylene, polypropylene, polymethylpentene and the like), polyester polymers (polyethylene terephthalate (PET), polyethylene naphthalate (PEN), and the like), polycarbonate polymers, and epoxy polymers.

The cell culture vessel 11 preferably includes, for example, a polymer including a dye structure (chromophore) that absorbs the laser or a laser absorbing layer formed of a photoacid generator that absorbs the laser and generates an acidic material, on the bottom surface of the inside (the cell 13 side in FIG. 1) of the cell culture vessel 11. As to the dye structure and the photoacid generator, reference can be made to, for example, the description of Japanese Patent No. 6033980. By providing the laser absorbing layer in the cell culture vessel 11, the energy of the laser can be converted into heat, acid, or the like when the laser projection unit of the cell treatment apparatus to be described below projects the laser, for example, thereby killing, liberating, or the like the cells present above the laser absorbing layer.

The cell 13 may be a cell, a cell mass composed of cells, a tissue, an organ, or the like. The cell may be, for example, a cultured cell or a cell isolated from a living body. The cell mass, the tissue, or the organ may be, for example, a cell mass, a cell sheet, a tissue, or an organ produced from the cells, or may be a cell mass, a tissue, or an organ isolated from a living body.

The observation unit 2 can observe the cells 13. Specifically, the observation unit 2 can observe the cells 13 in the cell culture vessel 11. As the observation unit 2, a known device for observing cells can be used, and specific examples thereof include an optical microscope and an electronic microscope. Examples of the optical microscope include a phase-contrast microscope, a differential interference contrast microscope, a polarization microscope, a fluorescence microscope, a confocal laser scanning microscope, a total internal reflection fluorescence microscope, a Raman microscope, a Coherent Anti-Stokes Raman Scattering (CARS) microscope, and a stimulated Raman scattering (SRS) microscope. When the observation unit 2 is the optical microscope, the observation moving unit 3 preferably includes a light source. The light source is not particularly limited, and can be determined appropriately depending on the type of the optical microscope, and specific examples thereof include halogen lamps, tungsten lamps, and white Light Emitting Diodes (LEDs). The location where the light source is placed is not particularly limited, and can be appropriately determined depending on the type of the optical microscope. As a specific example, the light source may be placed inside of the cell treatment chamber 1. When the light source is placed in the cell treatment chamber 1, the observation moving unit 3 preferably includes, for example, a light source moving unit that can move the light source. In this case, for example, when observing the cells 13 by the observation unit 2, the light source moving unit moves the light source so that the cells 13 can be observed by the observation unit 2 by irradiating the cells 13 with the illumination light emitted from the light source. The objective lenses 21a, 21b, and 21c are lenses that enlarge the image of the cell 13 to an intended magnification, for example. The objective lenses 21a, 21b, and 21c are switchable, for example. As the objective lenses 21a, 21b, and 21c, for example, known lenses or lens systems can be used and can be appropriately selected depending on an intended magnification. While the cell treatment apparatus 100 according to the present embodiment include three objective lenses 21, the cell treatment apparatus 100 may include one or two or more of the objective lenses (21a, 21b, and 21c). When the cell treatment apparatus 100 includes two or more objective lenses (21a, 21b, and 21c), it is preferable that each of the objective lenses 21 can enlarge the image to different magnifications. While the observation unit 2 includes three objective lenses (21a, 21b, 21c) in the cell treatment apparatus 100 according to the present embodiment, the objective lenses (21a, 21b, 21c) are optional and the observation unit 2 may or may not include them.

The observation unit 2 may, for example, be able to image the cells 13 in the cell culture vessel 11. In this case, the observation unit 2 includes, for example, an image sensor. As the image sensor, for example, a known image sensor can be used, and specific examples thereof include a Charge-Coupled Device (CCD) and a Complementary Metal Oxide Semiconductor (CMOS). The observation unit 2 images, for example, the cells 13 in a part of or the entire cell culture vessel 11. When the observation unit 2 images the cells 13 in the entire cell culture vessel 11, the observation unit 2 images the cells 13 in the entire cell culture vessel 11 at once or several times. When the observation unit 2 images the cells 13 several times, the cells 13 in the entire cell culture vessel 11 may be imaged by dividing the cell culture vessel 11 into a plurality of sections, and imaging the plurality of sections. The sections may be set so as not to overlap with one another, or may be set so as to partially overlap with one another, for example. The observation unit 2 images the sections at one time or with several times, for example. When the observation unit 2 can image the cells 13, the control unit 6 may store the obtained images, for example. The shapes of the sections are not particularly limited, and can be set appropriately depending on the shape of the field of view that can be observed or imaged by the observation unit 2. When each of the sections has a band shape, for example, a line scan camera or the like can be used as the observation unit 2. The observation unit 2 may, for example, acquire its position information. Examples of the position information include coordinates (two-dimensional coordinates) in the XY axes and coordinates (three-dimensional coordinates) in the XYZ axes. Imaging the cells 13 by the observation unit 2 is controlled by the control unit 6, for example, as described below.

The observation moving unit 3 can move the observation unit 2. The observation moving unit 3 may be, for example, a known moving unit (drive unit). The moving direction of the observation moving unit 3 is not particularly limited, and is, for example, any one direction, two directions, or all directions of the X-axis direction, the Y-axis direction, and the Z-axis direction. The observation moving unit 3 can move the observation unit 2 so that the observation unit 2 can observe or image a desired position in the cell culture vessel 11, for example. As described above, when the observation unit 2 includes a light source, the observation moving unit 3 may be able to move the light source, for example. The observation moving unit 3 may move the observation unit 2 and the light source by one moving unit, or may move them separately by two or more moving units, for example. The observation moving unit 3 may, for example, acquire its position information. Examples of the position information include coordinates (two-dimensional coordinates) in the XY axes and coordinates (three-dimensional coordinates) in the XYZ axes. When the observation moving unit 3 acquires the position information, the observation moving unit 3 may acquire the position information as the position information of the observation unit 2, for example. The observation moving unit 3 is only required to be placed so as to be able to move the observation unit 2, and may be placed appropriately depending on a moving unit to be used, for example. Moving the observation unit 2 by the observation moving unit 3 is controlled by the control unit 6, for example, as described below.

The laser projection unit 4 can project a laser image onto the cells 13. While the laser projection unit 4 includes a laser light source 41, a laser image generation portion 42, a projection optical system 43, and a housing 44 having an opening 45 in the cell treatment apparatus 100 of the present embodiment, the laser projection unit 4 is only required to be able to project a laser image generated by the laser image generation portion 42 onto the cells 13. In the cell treatment apparatus 100 according to the present embodiment, the laser light oscillated from the laser light source 41 passes through a lens 43a and then is converted into image light of a laser image to be projected onto the target cells 13a by the laser image generation portion 42, for example. The image light passes through the lens 43b and the opening 45 of the housing 44, and then is projected onto the target cells 13a, for example. The "laser image" refers to, for example, an image projected onto the cells 13 by the laser light. The "image light" refers to, for example, laser light modulated so as to be able to project the laser image onto the target cells 13a. The laser projection unit 4 may, for example, acquire its position information. Examples of the position information include coordinates (two-dimensional coordinates) in the XY axes and coordinates (three-dimensional coordinates) in the XYZ axes. The laser projection unit 4 is controlled by the control unit 6, for example, as described below.

The laser projection unit 4 projects the laser image onto the cells 13 by projecting the laser image onto a part of or the entire inside of the cell culture vessel 11, for example.

The laser projection unit 4 projects the laser image directly or indirectly onto the cells 13, for example. The "direct projection" refers to, for example, projecting laser light forming the laser image onto the cells 13. The "indirect projection" refers to, for example, projecting laser light forming the laser image onto a laser absorbing layer, which is placed adjacent to the cells 13 and absorbs the laser light. When the cell culture vessel 11 includes the laser absorbing layer to be described below, the laser projection unit 4 preferably projects the laser image onto the laser absorbing layer. The laser projection unit 4 may project a laser image onto the cells 13 by, for example, dividing a region where the laser image is to be projected into a plurality of sections and projecting a laser image that has been divided so as to correspond to each section onto each section. The laser image projected onto each section may also be referred to as, for example, a divided image. As described above, the cell treatment apparatus 100 according to the present embodiment divides the region onto which the laser image is to be projected into a plurality of sections and projects the laser image onto the cells 13, for example, whereby the cells 13 can be treated even in a region larger than a region onto which the laser image can be projected by the laser projection unit 4 at one time. The sections may be set so as not to overlap with one another, or may be set so as to partially overlap with one another, for example. The shapes of the sections are not particularly limited, and can be appropriately determined depending on the shapes of the taken images that can be projected by the laser projection unit 4. When each of the sections has a rectangular shape such as a band shape, the laser projection unit 4 may project the laser image continuously or discontinuously from one end to the other end, for example. In this case, the laser moving unit 5 to be described below moves the laser projection unit 4 continuously or discontinuously, for example, from one end to the other end.

The laser light source 41 is, for example, a device that oscillates a continuous wave laser or a pulsed laser. The laser light source 41 may be, for example, a high-frequency laser having a long pulse width close to a continuous wave. The output of the laser oscillated from the laser light source 41 is not particularly limited, and can be appropriately determined depending on, for example, treatment and cells. The wavelength of the laser oscillated by the laser light source 41 is not particularly limited, and can be, for example, a visible light laser, an infrared laser, or the like having a wavelength of 405 nm, 450 nm, 520 nm, 532 nm, 808 nm, or the like. As described above, when the laser absorbing layer is provided in the cell culture vessel 11, the laser light source 41 oscillates, for example, the laser having a wavelength that can be absorbed by the laser absorbing layer. Since the influence on the cells 13 can be suppressed, it is preferable that the laser light source 41 oscillate a laser having a wavelength longer than 380 nm. As a specific example, the laser light source 41 can be a continuous wave diode laser having a wavelength in the vicinity of 405 nm and a maximum output of 5 W.

While the laser image is projected by directly using the laser light oscillated from the laser light source 41 in the cell treatment apparatus 100 according to the present embodiment, the laser image may be projected by guiding the laser light using a light guiding unit and using the thus guided laser. Examples of the light guiding unit include an optical fiber, a mirror, and Micro Electro Mechanical Systems (MEMS). In this case, the cell treatment apparatus 100 according to the present embodiment includes, in addition to the laser light source 41, a laser emission unit that emits guided laser light, for example, and the laser light source 41 and the laser emission unit are optically connected to each other.

The laser image generation portion 42 generates a laser image to be projected onto the cells 13 from the laser light oscillated from the laser light source 41. The laser image generation portion 42 is only required to generate, for example, image light that forms a desired laser image when projected onto the cells 13 from the laser light. The laser image generation portion 42 may be, for example, a spatial modulator. The spatial modulator forms image light obtained by modulating the laser light in accordance with the laser image, for example. Examples of the spatial modulator include a digital micromirror device (DMD) and a liquid crystal panel. The laser image generation portion 42 is controlled by the control unit 6, for example, as described below. When the laser image generation portion 42 is the DMD, the DMD projects a laser image onto the cells 13 by changing the intensity distribution of a part of or all of the laser light oscillated from the laser light source 41, and more specifically, by reflecting a part of or all of the laser light toward the cells 13. When the laser image generation portion 42 is a liquid crystal panel, the liquid crystal panel projects a laser image onto the cells 13 by transmitting a part of or all of the laser light oscillated from the laser light source 41 toward the cells 13. The cell treatment apparatus 100 according to the present embodiment does not directly project the laser light oscillated from the laser light source 41 onto the cells 13, but generates a laser image to be projected onto the cells 13 from the laser light by the laser image generation portion 42, and projects this laser image.

The projection optical system 43 is, for example, an optical system for guiding laser light from the laser light source 41 to the cells 13 in the cell culture vessel 11. In the cell treatment apparatus 100 according to the present embodiment, the projection optical system 43 includes two lenses 43a and 43b. The lens 43a may also be referred to as a light source lens, for example. The light source lens is, for example, a lens for condensing laser light projected from the laser light source 41. The light source lens can be, for example, a known lens or lens system, and is preferably a lens or lens system that provides Kohler illumination that can uniformly illuminate the plane on which the cell 13 or the laser absorbing layer is present. The lens 43b can also be referred to as, for example, a projection lens. The projection lens is, for example, a lens for projecting image light of the laser image onto the cells 13. The projection lens can be, for example, a known lens or lens system. The projection optical system 43 may include other components including: a lens such as a relay lens, a fly's eye lens, a rod lens, a diffuser plate, or the like; a prism such as a total internal reflection prism (TIR prism) or the like; and a mirror, for example.

While the laser light source 41, the laser image generation portion 42, and the projection optical system 43 configuring the laser projection unit 4 are accommodated in the housing 44 in the present embodiment, the laser image generation portion 42 and the projection optical system 43 may not be accommodated in the housing 44. While the housing 44 has the opening 45 in the cell treatment apparatus 100 according to the present embodiment, the housing 44 may not have the opening 45. In this case, it is preferable that the housing 44 have, for example, a translucent portion through which the laser image can be projected. The translucent portion is formed of, for example, the translucent member.

The laser moving unit 5 can move the laser projection unit 4. The laser moving unit 5 may be, for example, a known moving unit (drive unit). The moving direction of the laser moving unit 5 is not particularly limited, and is, for example, any one direction, two directions, or all directions of the X-axis direction, the Y-axis direction, and the Z-axis direction. The laser moving unit 5 can move the laser projection unit 4 so that the laser projection unit 4 can project a laser image onto the cells 13 at a desired position in the cell culture vessel 11. For example, the laser moving unit 5 may move any one or more of the components of the laser projection unit 4 by a moving unit, or may move two or more components separately by a moving unit. The laser moving unit 5 may, for example, acquire its position information. Examples of the position information include coordinates (two-dimensional coordinates) in the XY axes and coordinates (three-dimensional coordinates) in the XYZ axes. When the laser moving unit 5 acquires the position information, the laser moving unit 5 may acquire the position information as the position information of the laser projection unit 4, for example. The laser moving unit 5 is only required to be placed so as to be able to move the laser projection unit 4, and may be appropriately placed depending on a moving unit to be used, for example. Moving the laser projection unit 4 by the laser moving unit 5 is controlled by the control unit 6, for example, as described below.

Figure 2:
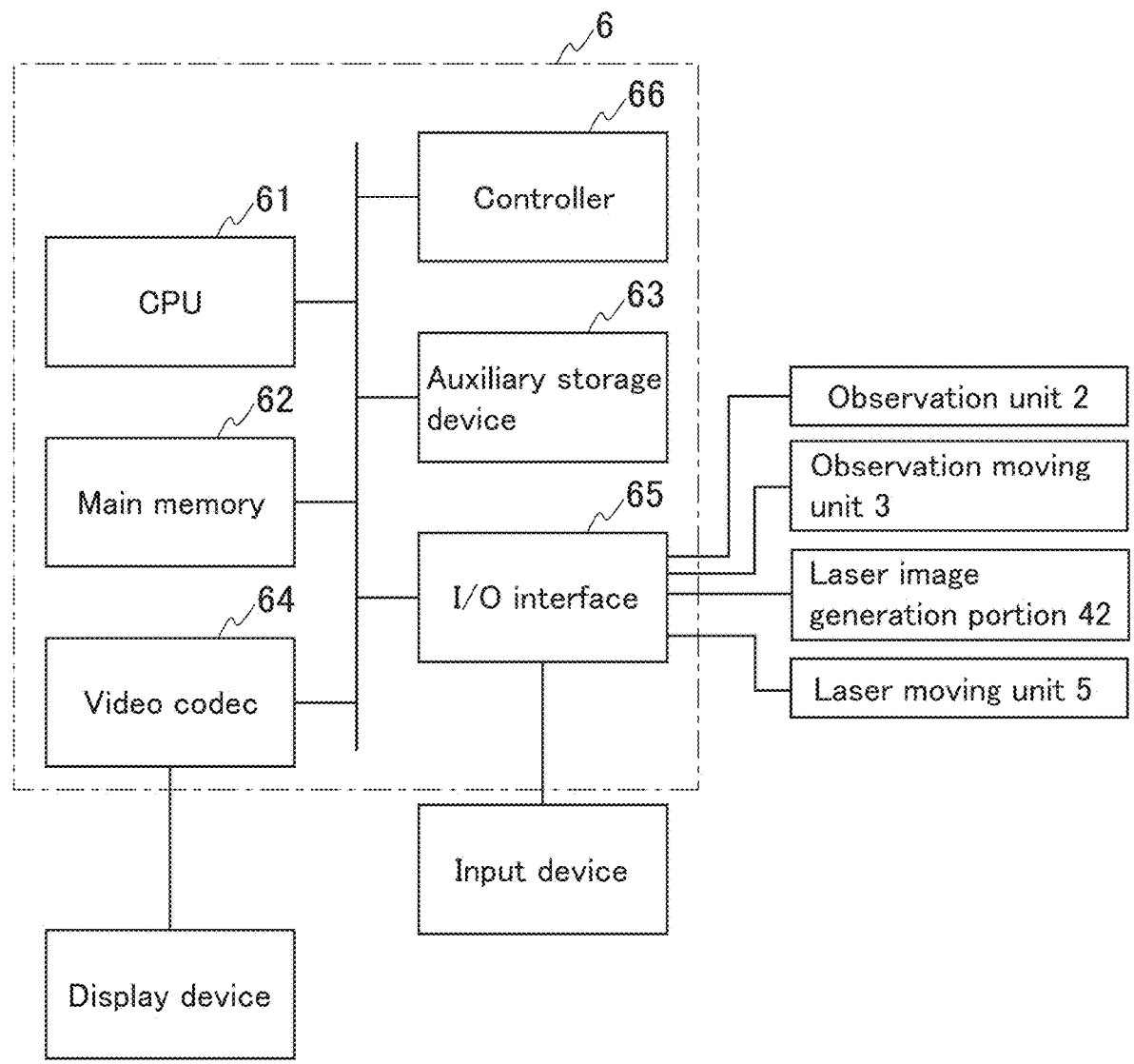
FIG. 2 is a block diagram showing an example of a control unit in the cell treatment apparatus according to the first embodiment.

The control unit 6 has a configuration similar to a personal computer, a server computer, a workstation, or the like. FIG. 2 is a block diagram showing an example of a control unit 6 in the cell treatment apparatus 100 according to the present embodiment. As shown in FIG. 2, the control unit 6 includes a central processing unit (CPU) 61, a main memory 62, an auxiliary storage device 63, a video codec 64, an input-output (I/O) interface 65, and the like, which are controlled by a controller (a system controller, an I/O controller, or the like) 66 and operate in cooperation with each other. The auxiliary storage device 63 can be a storage device such as a flash memory, a hard disk drive, or the like. The video codec 64 includes: a graphics processing unit (GPU) that generates a screen to be displayed based on a drawing instruction received from the CPU 61 and transmits the screen signal to a display device or the like outside the cell treatment apparatus 100; and a video memory that temporarily stores the screen and image data, for example. The I/O interface 65 is a device that can communicate with and control the units such as the observation unit 2, the observation moving unit 3, the laser image generation portion 42, and the laser moving unit 5. The I/O interface 65 may include a servo driver (servo controller). The I/O interface 65 may be connected to an input unit outside the cell treatment apparatus 100, for example. The display device may be, for example, monitors (for example, various image display devices such as a liquid crystal display (LCD) and a cathode ray tube (CRT) display) that output images. Examples of the input device include a touch panel, a track pad, a pointing device such as a mouse, a keyboard, and a push button that can be operated by a finger of a user.

The programs executed by the control unit 6 and the respective pieces of information are stored in the auxiliary storage device 63. The program is read into the main memory 62 and is decoded by the CPU 61 at the time of executing the program. The control unit 6 controls each member according to the program. The control of each member by the control unit 6 will be described below.

In the cell treatment apparatus 100 according to the present embodiment, the control unit 6 has the functions of controlling the observation unit 2, the observation moving unit 3, the laser image generation portion 42, and the laser moving unit 5, so that a control unit does not have to be individually provided in each member, whereby the device can be miniaturized. The present invention, however, is not limited thereto. In the cell treatment apparatus 100 of the present embodiment, for example, a control unit as the control unit 6 may be provided in each of the observation unit 2, the observation moving unit 3, the laser image generation portion 42, and the laser moving unit 5, and each member may be controlled by the control unit of each member. The cell treatment apparatus 100 according to the present embodiment may include, for example, the control unit 6 and the control units of the respective members to control the members in cooperation. The control unit 6 may be configured by one semiconductor element, may be a chip in which a plurality of semiconductor elements are packaged, or may be a substrate on which a plurality of semiconductor elements are provided.

Next, the operation of the control unit 6 in the cell treatment apparatus 100 according to the present embodiment and the method for treating cells using the cell treatment apparatus 100 will be described.

The control unit 6 controls the generation of a laser image by the laser image generation portion 42. Specifically, the control unit 6 stores, for example, laser image information associating the position of the laser projection unit 4 with the laser image to be projected onto the cells 13 at the position of the laser projection unit 4. The control unit 6 acquires the laser position information, which is the position of the laser projection unit 4, and controls the laser image generation portion 42 to generate a laser image associated with the position of the laser projection unit 4, based on the laser position information and the laser image information. Thus, for example, the control unit 6 first acquires the laser image information, and stores the laser image information in the auxiliary storage device 63 of the control unit 6. The laser image information may be, for example, information acquired in advance by an observing device, a cell treatment apparatus, or the like for other cells, information input by a user of the cell treatment apparatus 100 according to the present embodiment, or information acquired by the cell treatment apparatus 100 according to the present embodiment. Among them, the information acquired by the cell treatment apparatus 100 according to the present embodiment is preferable because it allows the cells 13 to be treated more accurately.

Figure 3:
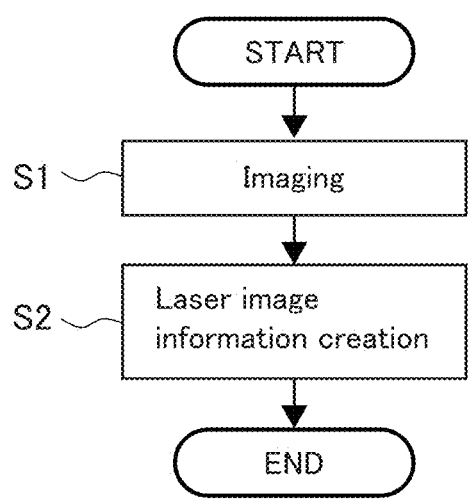
FIG. 3 is a flow chart showing the process of acquiring laser image information using the cell treatment apparatus according to the first embodiment.

When acquiring the laser image information using the cell treatment apparatus 100 of the present embodiment, the laser image information is acquired, for example, as follows. FIG. 3 is a flow chart showing the process of acquiring the laser image information using the cell treatment apparatus 100 of the present embodiment. As shown in FIG. 3, acquiring the laser image information includes a step S1 (imaging) and a step S2 (laser image information creation).

First, in the imaging step (S1), the cell culture vessel 11 containing the cells 13 placed in the cell treatment apparatus 100 is imaged. Specifically, the control unit 6 controls the observation unit 2 and the observation moving unit 3 to acquire an image containing the cells 13 and the observing position information, which is the position of the observation unit 2, at the time of acquiring the image. At this time, the control unit 6 images a part of or the entire (target region) cell culture vessel 11 by the observation unit 2. The control unit 6 may divide the target region in the cell culture vessel 11 into a plurality of sections, and may control the observation unit 2 and the observation moving unit 3 to image the plurality of sections. When imaging the plurality of sections, the control unit 6 may integrate the images of the sections. As described above, by dividing the target region into a plurality of sections and imaging the plurality of sections, even in the case where the cell culture vessel 11 is large or the region to be imaged is larger than the region that can be imaged by the observation unit 2 at one time, the imaging can be performed efficiently. When the control unit 6 images the entire cell culture vessel 11 by the observation unit 2, it is preferable to integrate the images of the sections to acquire the image of the entire cell culture vessel 11. The method for integrating the images of the respective sections is not particularly limited, and can be performed by a known image processing method. For example, the control unit 6 may give the position information to the pixels of the taken image based on the observation position information. When the observation unit 2 includes a line camera, the target region may be divided into a plurality of sections having predetermined widths that can be imaged by the line camera, and the plurality of sections may be imaged in the imaging step. When the observation unit 2 includes a high-resolution image sensor, imaging may be performed such that the target region falls within a single field of view in the imaging step.

Next, in the laser image information creating step (S2), the laser image information is created based on the image and the observing position information obtained by the observation unit 2. Specifically, the control unit 6 detects the target cells 13*a* and the non-target cells 13*b* in the image obtained by the observation unit 2, and creates a laser image defining the presence or absence and/or the intensity of the projection of the laser light with the region where the cells 13*a* are present as the projection region of the laser light and the region where the cells 13*b* are present as the non-projection region of the laser light. The method for detecting the cells 13*a* and 13*b* in the image acquired by the observation unit 2 is not particularly limited, and can be performed by a known cell discrimination method. As a specific example, the method for detecting the cells 13*a* and 13*b* may be a method of using a learned model obtained by performing depth learning so as to be able to detect the cells 13*a* and 13*b*. The cells 13*a*, 13*b* may be detected, for example, by a user of the cell treatment apparatus 100 inputting with the input device. The laser image may be created, for example, by detecting either one of the target cells 13*a* and the non-target cells 13*b*. Then, when the observation position information and the laser position information, which is the position of the laser projection unit 4 to be described below, are the same coordinate plane, the control unit 6 gives the position information to the pixels of the laser image based on the observation position information, thereby creating the laser image information associating the laser position information with the laser image. On the other hand, when the observation position information and the laser position information to be described below are different coordinate planes, the control unit 6 converts the observation position information into the position information of the coordinate plane of the laser position information, and then gives the converted position information to the pixels of the laser image, thereby creating laser image information associating the laser position information with the laser image. In this manner, the control unit 6 can acquire the laser image information. Then, the control unit 6 stores the laser image information in the auxiliary storage device 63.

When the laser projection unit 4 divides the region to which the laser image is to be projected into sections and projects a laser image which has been divided so as to correspond to each section, the control unit 6 divides the laser image into divided images corresponding to the sections (for example, having predetermined widths). Then, when the observation position information and the laser position information, which is the position of the laser projection unit 4 to be described below, are the same coordinate plane, the control unit 6 gives the position information to the pixels of the divided image based on the observation position information, thereby creating divided image information, which is the laser image information, associating the laser position information with the divided image. On the other hand, when the observation position information and the laser position information are different coordinate planes, the control unit 6 converts the observation position information into the position information of the coordinate plane of the laser position information, and then gives the converted position information to the pixels of the divided image, thereby creating divided image information, which is the laser image information, associating the laser position information with the divided image. In this manner, the control unit 6 can acquire the laser image information. Then, the control unit 6 stores the laser image information in the auxiliary storage device 63.

Next, when treating the cells using the cell treatment apparatus 100 according to the present embodiment and the laser image information, the cell treatment can be performed, for example, in the S3 step (laser treatment) as described below.

In the laser treatment step, the laser image is projected onto the cells 13 by the laser projection unit 4 based on the laser position information, which is the position information of the laser projection unit 4, and the laser image information. Specifically, the control unit 6 first acquires the laser position information. Next, based on the laser position information and the laser image information, it is judged whether there is a laser image associated with the present position of the laser projection unit 4. In the case of No, the control unit 6 moves the laser projection unit 4 with the laser moving unit 5. On the other hand, in the case of Yes, the control unit 6 reads the associated laser image and controls the laser image generation portion 42 to generate the associated laser image as a laser image to be projected onto the cells 13 from the laser light oscillated from the laser light source 41. The laser projection unit 4 projects the associated laser image onto the cells 13, thereby treating the target cells 13a. The projection time of the laser image is not particularly limited, and can be appropriately determined according to, for example, the type of treatment to be performed. Such a treatment is repeatedly performed until the treatment for the target cells 13a in the cell culture vessel 11 is completed, whereby the treatment for the cells in the cell culture vessel 11 can be performed. In the laser treatment step, for example, the laser image is projected onto the cells in a part of or the entire cell culture vessel 11.

Figure 4A:
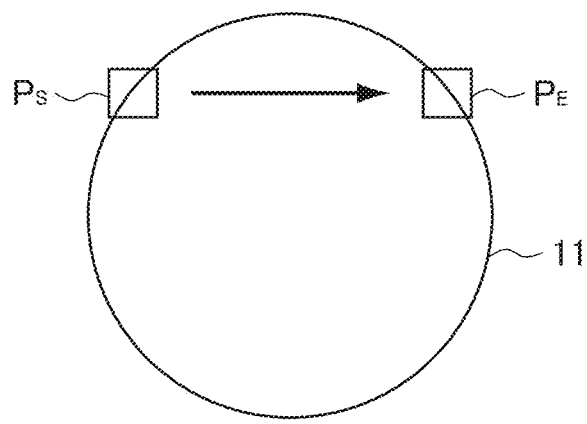
FIG. 4A is a view showing an example of a movement of a laser moving unit in the cell treatment apparatus according to the first embodiment.
Figure 4B:
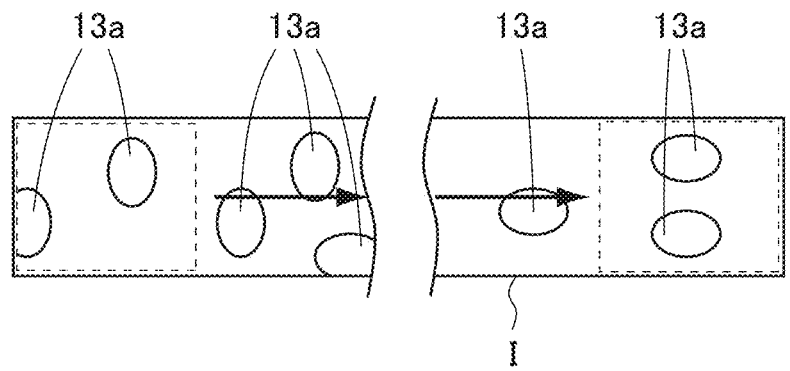
FIGS. 4B and 4C are views showing the order of reading laser images in the cell treatment apparatus according to the first embodiment.
Figure 4C:
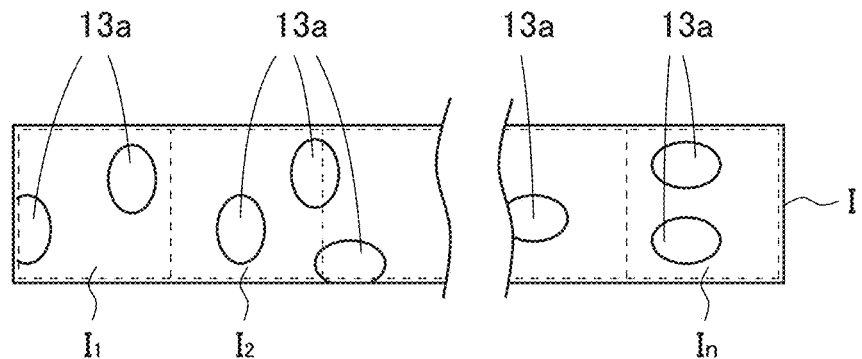

In the laser treatment step, for example, as shown in FIG. 4A, the control unit 6 preferably controls the laser moving unit 5 to move from the projection start position $P_S$ of the laser image at one end of the cell culture vessel 11 to the laser projection end position $P_E$ at the other end of the cell culture vessel 11. The laser moving unit 5 preferably moves substantially linearly as indicated by the arrow in FIG. 4A, for example. When the laser moving unit 5 moves from the projection start position $P_S$ to the laser projection end position $P_E$, it is preferable that the control unit 6 controls the laser projection unit 4 to project the associated laser image from the projection start position of the laser image at one end of the cell culture vessel 11 to the projection end position of the laser image at the other end of the cell culture vessel 11. By adopting such a configuration, the control unit 6 controls the laser moving unit 5 to move, so that the time for searching for the region where the target cells 13a are present can be suppressed, whereby the cells 13a in the cell culture vessel 11 can be more efficiently treated. Thus, the cell treatment apparatus 100 can further suppress a variation of the treatment time of treating the cells. The laser projection unit 4 projects, for example, the associated laser image continuously or discontinuously. When the laser projection unit 4 continuously projects the associated laser image, the control unit 6 controls the laser moving unit 5 to continuously move, for example. Preferably, the laser moving unit 5 moves the laser projection unit 4 from the projection start position to the projection end position at a substantially equal speed or at an equal speed. The cell treatment apparatus 100 can thereby keep the quantity of laser projected onto the target cells 13a constant. The control unit 6 continuously reads the region indicated by the broken line in FIG. 4B from one end toward the other end along the arrow direction in the associated laser image I, for example. The control unit 6 controls the laser image generation portion 42 to generate, for example, readout laser image. Thereby, the laser projection unit 4 can project the laser image corresponding to the position of the laser projection unit 4 from the projection start position to the projection end position. The region indicated by the broken line indicates, for example, the region onto which the laser can be projected by the laser projection unit 4 at once. On the other hand, when the laser projection unit 4 projects the associated laser image discontinuously, the control unit 6 controls the laser moving unit 5 to move discontinuously, for example. Specifically, the control unit 6 moves laser projection unit 4 to the position of the laser position information $P_1, P_2, \ldots, P_n$ by the laser moving unit 5, for example. At this time, after moving the laser projection unit 4 to the position of the laser position information $P_m$ (m: integers of 1 to n) by the laser moving unit 5, the control unit 6 may stop the movement of the laser projection unit 4 by the laser moving unit 5 for a predetermined time, for example. The predetermined time may be set appropriately, for example, in accordance with the projection time of the laser image (image light) by the laser projection unit 4. The control unit 6 reads the laser images $I_1, I_2, \ldots, I_n$ associated with the laser position information $P_1, P_2, \ldots, P_n$, as shown in FIG. 4C, for example. The control unit 6 controls the laser image generation portion 42 to generate the associated laser images $I_1, I_2, \ldots, I_n$ when the laser projection unit 4 is moved to the $P_1, P_2, \ldots, P_n$ position, which is the position associated with the laser image, by the laser moving unit 5, for example.

Figure 5:
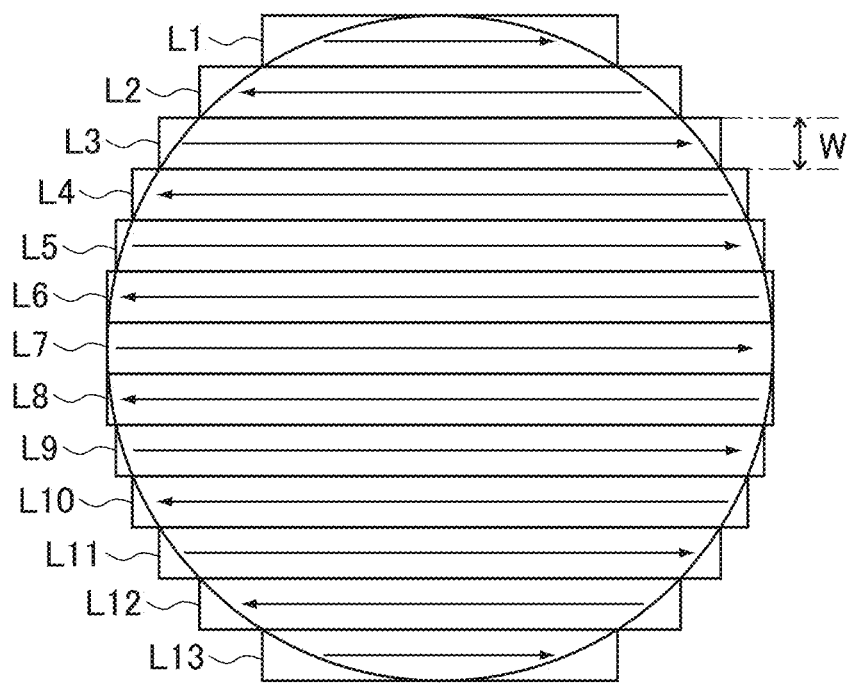
FIG. 5 is a view showing the order of projecting divided images by a laser projection unit in the cell treatment apparatus according to the first embodiment.

When the laser image information is divided image information associating the laser position information with the divided image, the control unit 6 may project divided images, as shown in FIG. 5. Specifically, the control unit 6 controls the laser moving unit 5 to move continuously or discontinuously from the projection start position of the divided image at one end of the cell culture vessel 11 to the projection end position of the divided image at the other end of the cell culture vessel 11 along the arrow direction, as indicated by L1 in FIG. 5. The control unit 6 reads, for example, the associated divided image L1 continuously or discontinuously. Then, the control unit 6 controls the laser image generation portion 42 to generate, for example, the readout divided image. Next, the control unit 6 moves, for example, the laser moving unit 5 in a direction substantially orthogonal to the moving direction of the laser moving unit 5. The distance traveled in the substantially orthogonal direction is, for example, the width of the divided image L1 (the length W in the vertical direction in FIG. 5). By setting such a width, the cell treatment apparatus 100 can prevent the laser image from projecting onto the cells 13 several times, and therefore can prevent the non-target cell 13b from being damaged, for example. Further, the control unit 6 controls the laser moving unit 5 to move continuously or discontinuously from the projection start position of the divided image at one end of the cell culture vessel 11 to the projection end position of the divided image at the other end of the cell culture vessel 11 along the arrow direction, as indicated by L2 in FIG. 5. The control unit 6 reads, for example, the associated divided image L2 continuously or discontinuously. Then, the control unit 6 controls the laser image generation portion 42 to generate, for example, the readout divided image. When treating the cells 13 in the entire cell culture vessel 11, the control unit 6 repeats the same operation until the projection of the divided image L13 by the laser moving unit 5 is completed. The reading and projecting of the divided images L1 to L13 can be performed, for example, in the same manner as the reading and projecting of the laser image I. By adopting such a configuration, the cells 13a that are present in a certain region or the entire region of the cell culture vessel 11 can be treated more efficiently. Thus, a variation of the treatment time of treating the cells can be suppressed.

Since the cell treatment apparatus 100 according to the present embodiment projects the laser images, different from direct irradiation of laser light which is point-irradiation, the laser light can be irradiated planarly. In the case of direct irradiation of the laser light, if the number of target cells 13a varies greatly, the area to be irradiated with the laser light also varies greatly, and therefore, the irradiation time of the laser light varies greatly. That is, the treatment time varies greatly. On the other hand, when the laser light is irradiated planarly as in the cell treatment apparatus 100 of the present embodiment, even if the number of the target cells 13a varies greatly, it is only necessary to change the position where the laser light is irradiated (the position where the cells 13a are present) and the position where the laser light is not irradiated (the position where the cells 13b are present) in the laser image, and the area where the laser image is projected by a single projection does not vary. Thus, according to the cell treatment apparatus 100 of the present embodiment, it is possible to suppress the variation of the treatment time of treating the cells 13a using the laser light, as compared to the case of direct irradiation of the laser light. The same effects can be obtained in the cell treatment apparatus described below.

Second Embodiment

Figure 6:
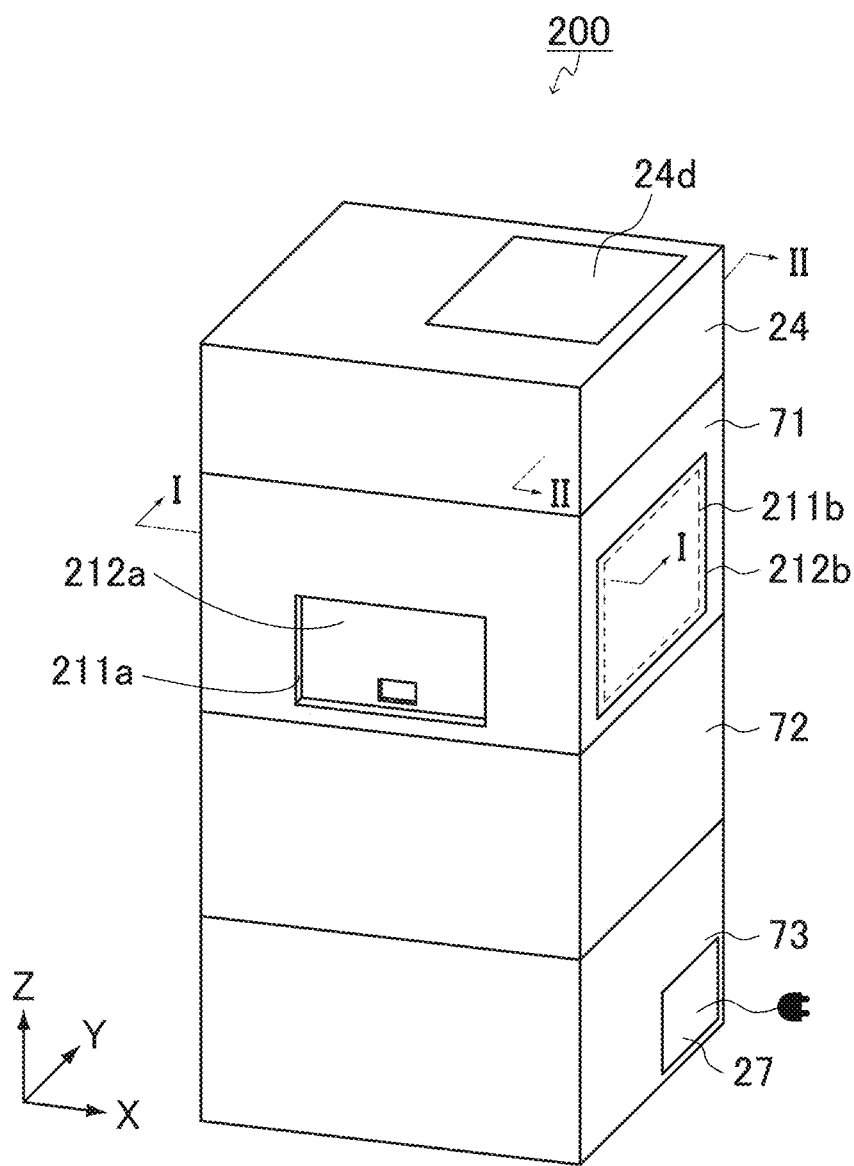
FIG. 6 is a perspective view showing an example of a cell treatment apparatus according to the second embodiment.
Figure 7:
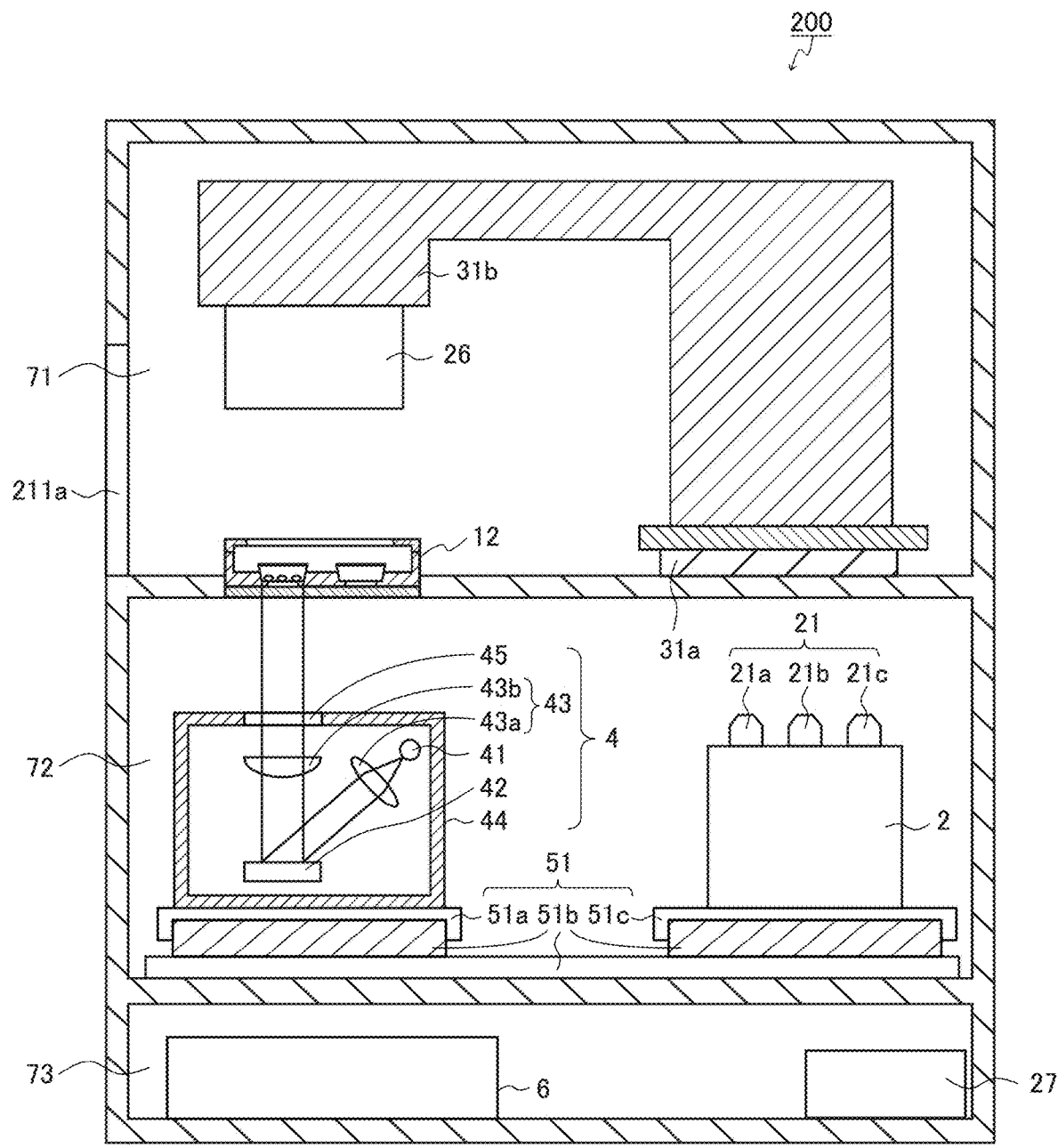
FIG. 7 is a schematic view showing an example of a cell treatment apparatus according to the second embodiment.
Figure 8:
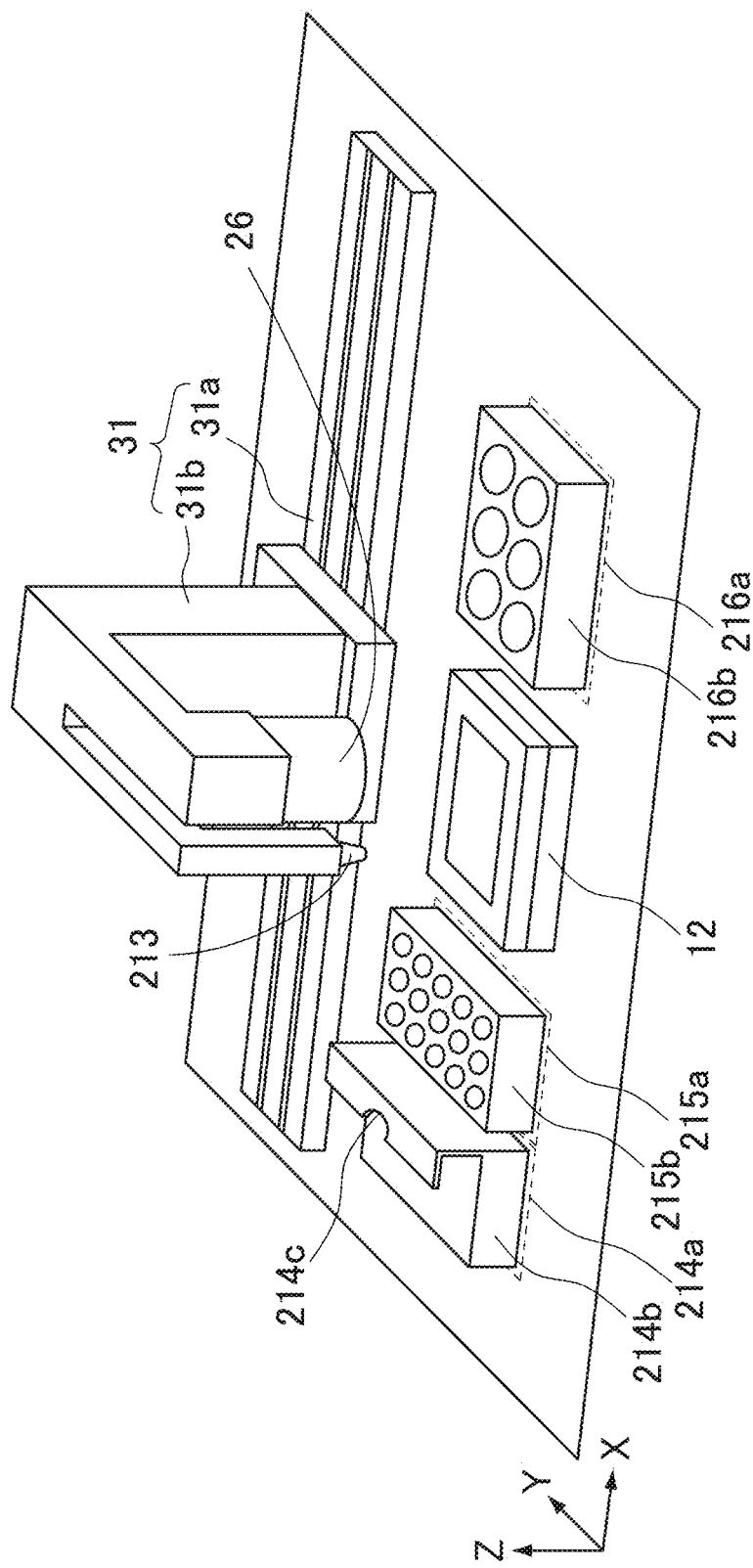
FIG. 8 is a perspective view showing an example of a first region in the cell treatment apparatus according to the second embodiment.
Figure 9:
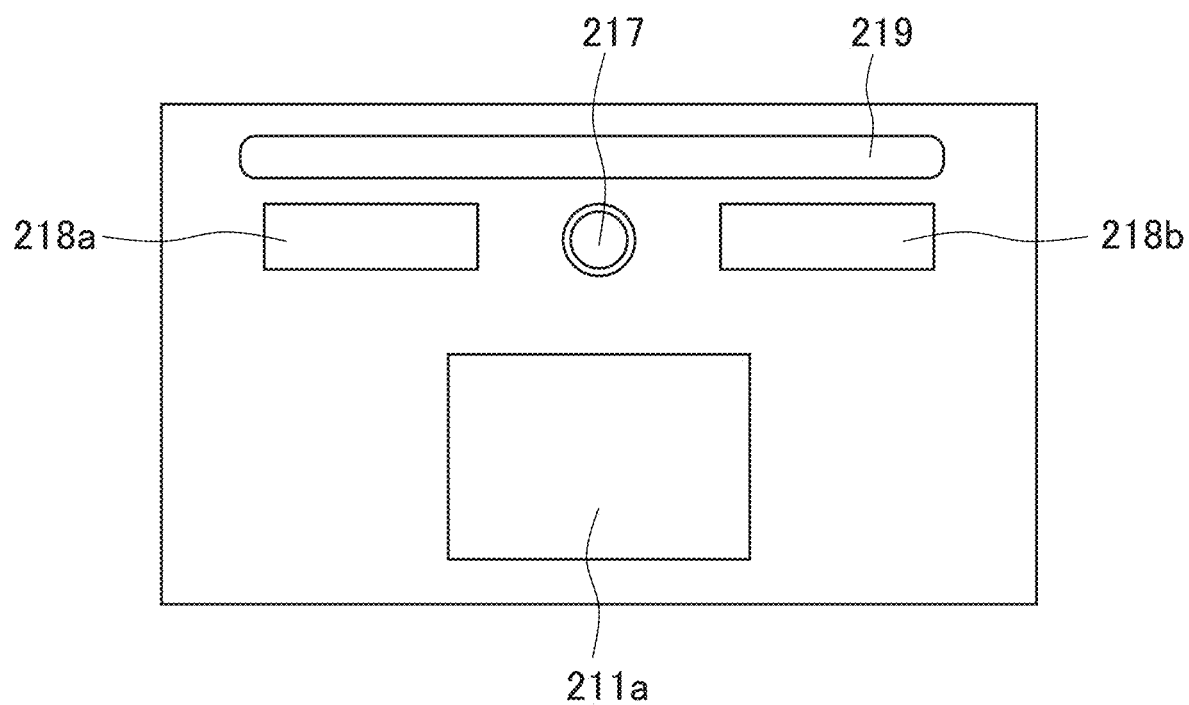
FIG. 9 is a cross-sectional view of the first region taken along the line I-I of FIG. 6.
Figure 10A:
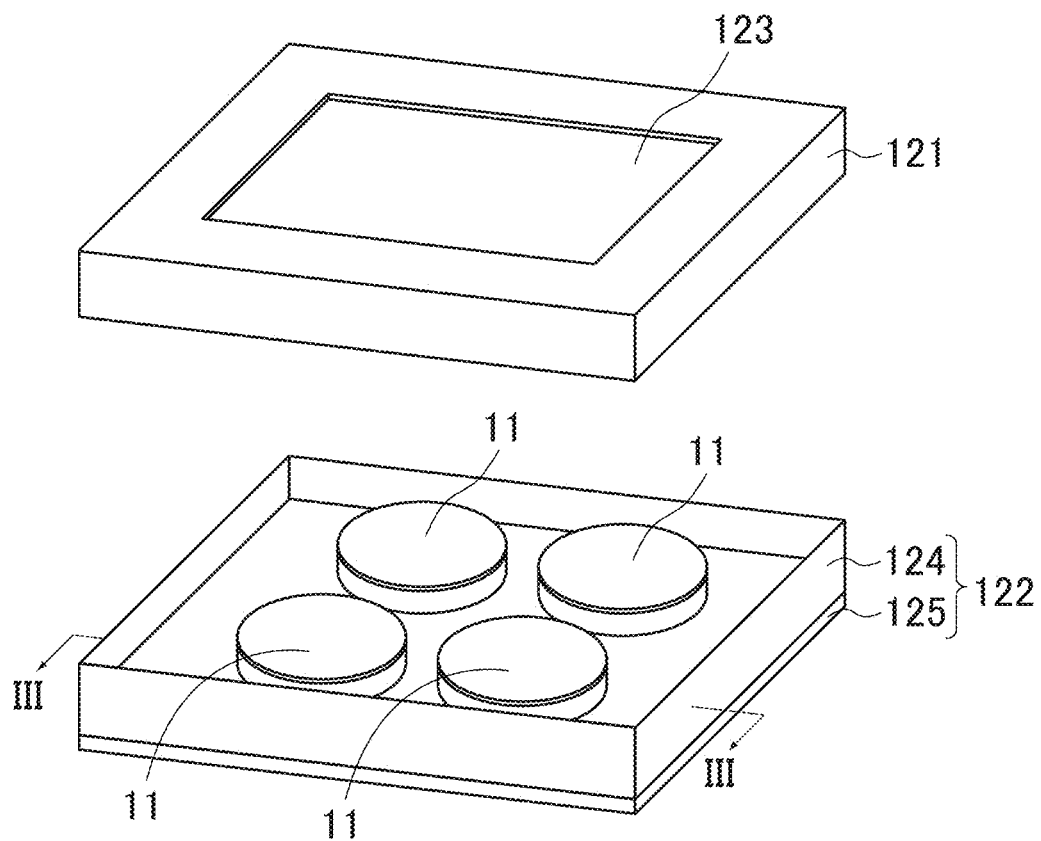
FIG. 10A is an exploded perspective view showing an example of a culture vessel placement portion in the cell treatment apparatus according to the second embodiment.
Figure 10B:
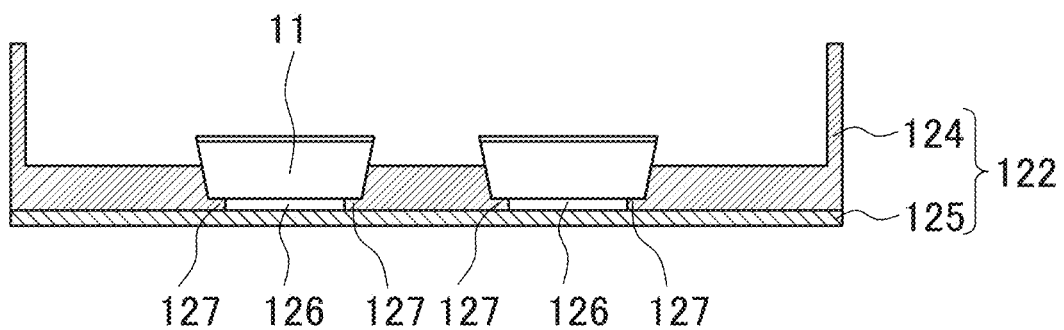
FIG. 10B is a cross-sectional view taken along the line III-III of FIG. 10A.
Figure 11:
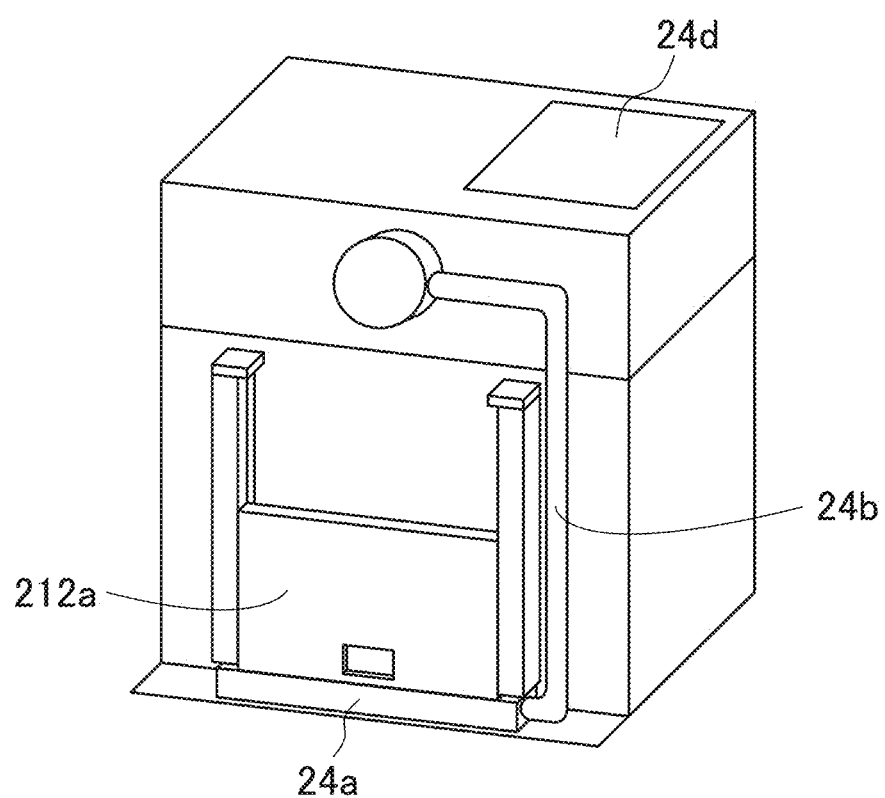
FIG. 11 is a perspective view showing an example of a first region and an example of a circulator in the case where an outer wall of the first region has been removed in the cell treatment apparatus according to the second embodiment.
Figure 12:
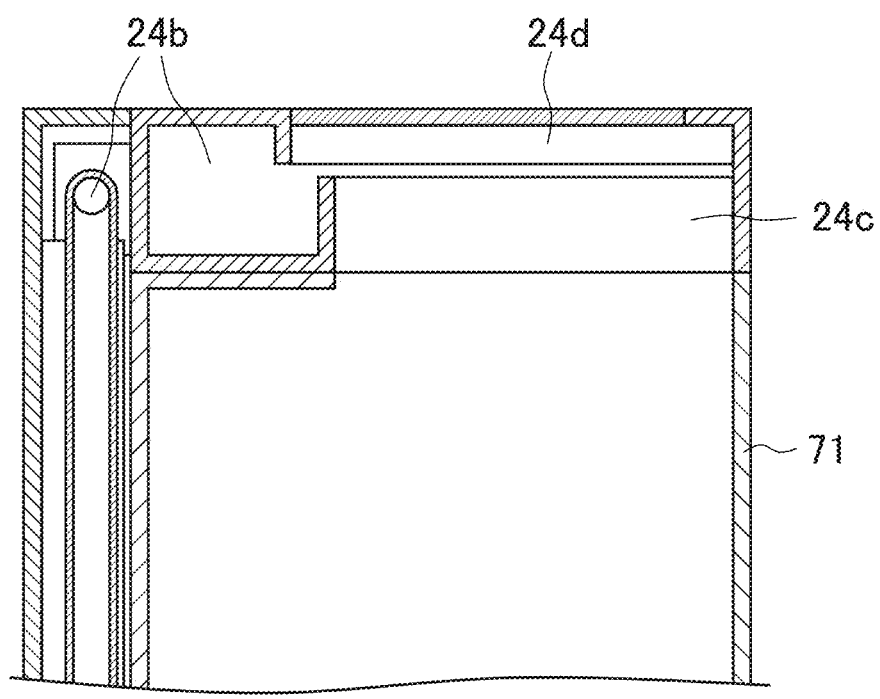
FIG. 12 is a cross-sectional view showing an upper part of the first region and the circulator taken along the line II-II of FIG. 6.
Figure 13A:
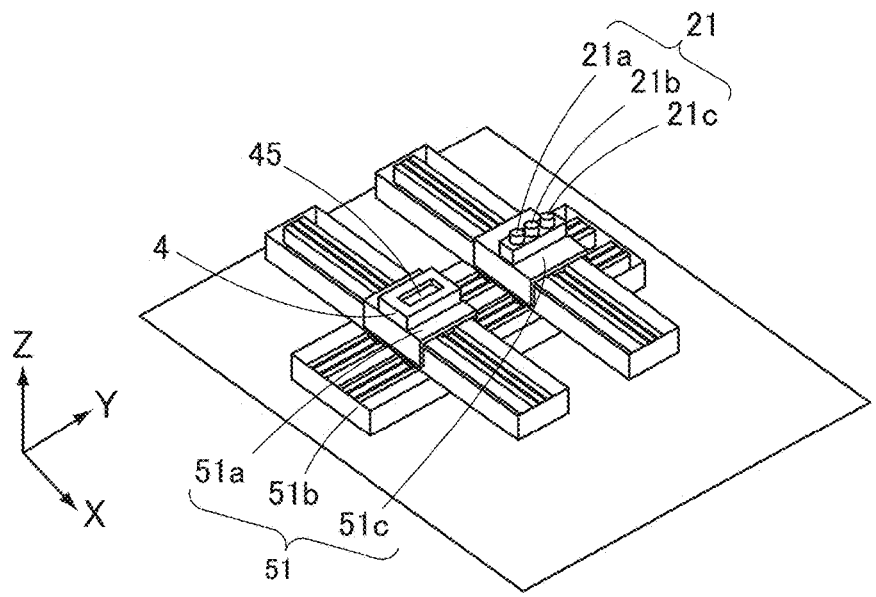
FIG. 13A is a perspective view showing an example of a configuration of a second region in the cell treatment apparatus according to the second embodiment.
Figure 13B:
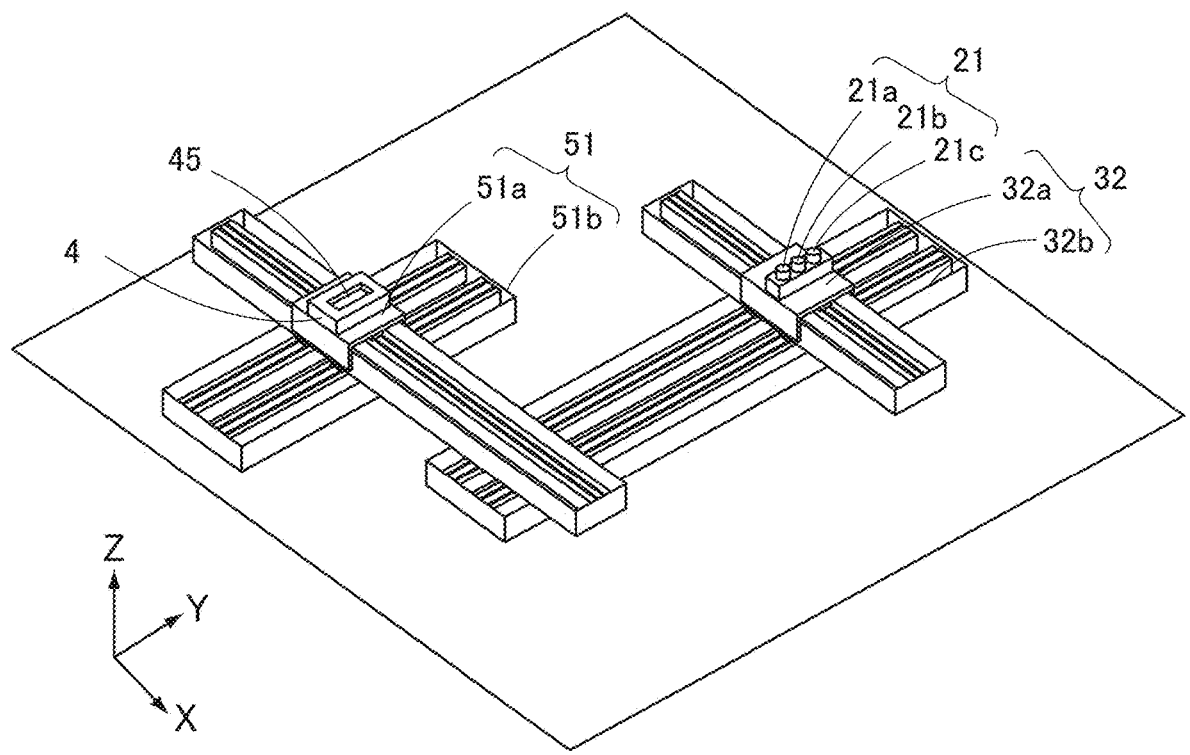
FIG. 13B is a perspective view showing another example of a configuration of the second region.
Figure 14:
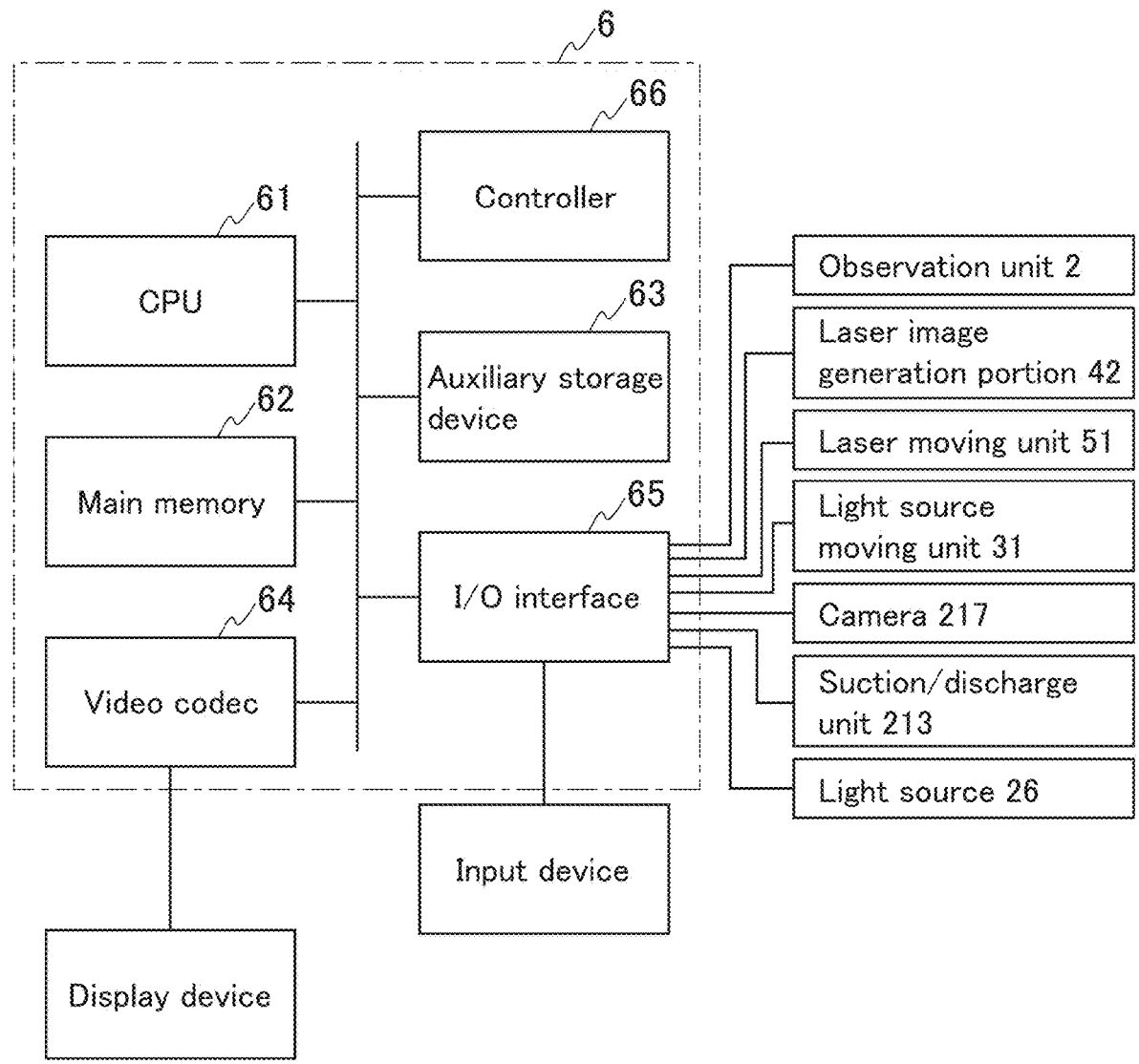
FIG. 14 is a block diagram showing an example of a configuration of a control unit in the cell treatment apparatus according to the second embodiment.
Figure 15:
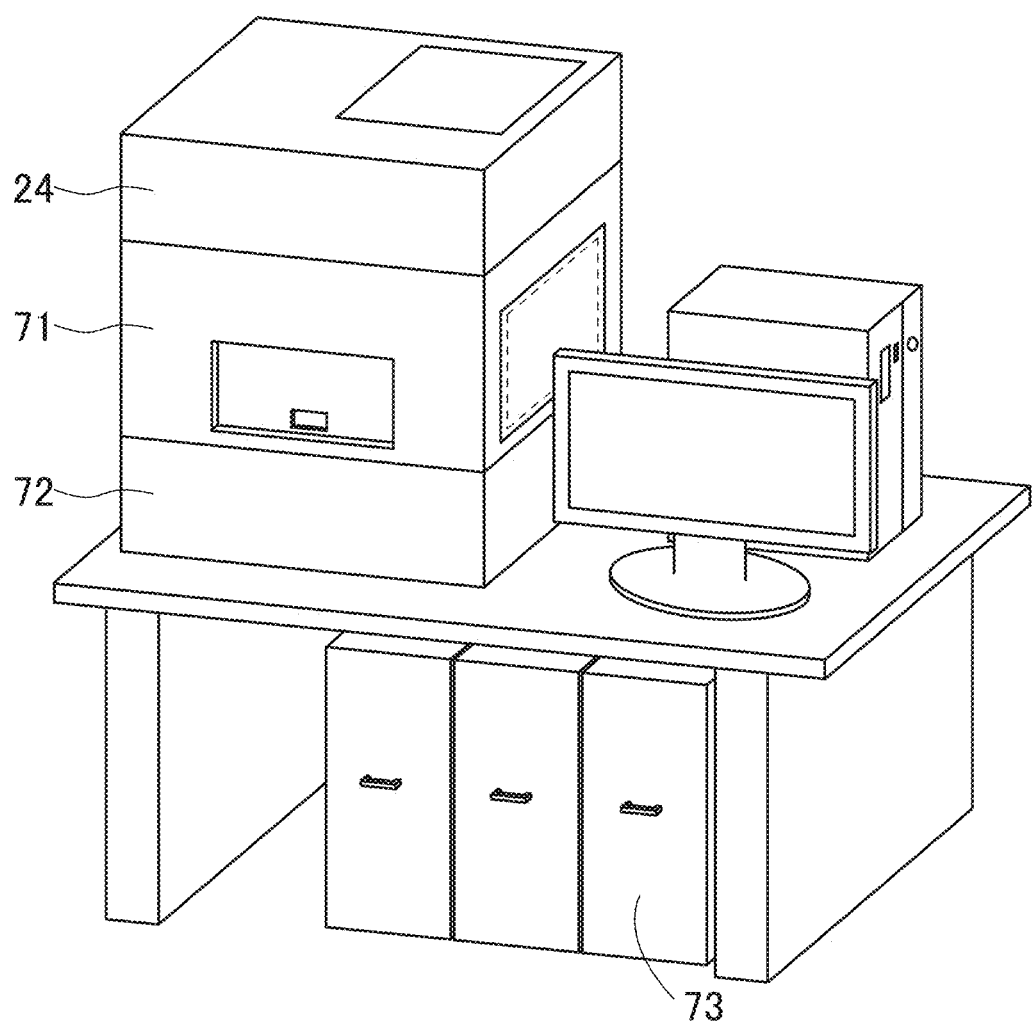
FIG. 15 is a perspective view showing another example of a cell treatment apparatus according to the second embodiment.

The present embodiment relates to an example of a cell treatment apparatus. FIGS. 6 to 15 each show an example of a configuration of the cell treatment apparatus according to the present embodiment. FIG. 6 is a perspective view showing an example of a configuration of the cell treatment apparatus according to the present embodiment, FIG. 7 is a schematic cross-sectional view showing the configurations of the first region, the second region, and the third region in the cell treatment apparatus according to the present embodiment, FIG. 8 is a perspective view showing an example of a configuration of the first region in the cell treatment apparatus according to the present embodiment, FIG. 9 is a cross-sectional view of the first region taken along the line I-I of FIG. 6, FIG. 10A is an exploded perspective view showing an example of a culture vessel placement portion in the cell treatment apparatus according to the present embodiment, FIG. 10B is a cross-sectional view taken along the line III-III of FIG. 10A, FIG. 11 is a perspective view of the first region and the circulator in the case where the outer wall of the first region is removed, FIG. 12 is a cross-sectional view of the upper part of the first region and the circulator taken along the line II-II of FIG. 6, FIG. 13A is perspective view showing an example of a configuration of the second region in the cell treatment apparatus according to the present embodiment, FIG. 13B is a perspective view showing another example of a configuration of the second region, Fig. FIG. 14 is a block diagram showing an example of a control unit in the cell treatment apparatus according to the present embodiment, and FIG. 15 is a perspective view showing another example of a configuration of the cell treatment apparatus according to the present embodiment.

As shown in FIG. 6, the cell treatment apparatus 200 according to the present embodiment includes a first chamber 71 (hereinafter may be referred to as "cell treatment chamber 1") as the first region, a second chamber 72 as the second region, a third chamber 73 as the third region, and a circulator 24, and the first chamber 71, the second chamber 72, and the third chamber 73 are placed in this order continuously from the top downward. While the cell treatment apparatus 200 according to the present embodiment includes the circulator 24, the circulator 24 is optional, and the cell treatment apparatus 200 may or may not include the circulator 24. As to the positional relationship among the first chamber 71, the second chamber 72, and the third chamber 73, it is only required that the first chamber 71 and the second chamber 72 are placed contiguously (adjacent to each other), and the third chamber 73 may be placed at any position. The third chamber 73 may be placed separately from the first chamber 71 and the second chamber 72, for example, as shown in FIG. 15. When the third chamber 73 is placed separately from the first chamber 71 and the second chamber 72 as shown in FIG. 15, the cell treatment apparatus 200 may be also referred to as, for example, a cell treatment system. The cell treatment system may, for example, be a tabletop system. The material for forming each region is not particularly limited, and examples thereof include a stainless steel plate, a rust-proof iron plate, and a resin plate that can be molded by vacuum molding, injection molding, pressure molding, or the like. The material for forming each region is preferably a non-translucent material so that the cells 13 in the cell culture vessel 11 can be imaged more clearly by the observation unit to be described below. The term "non-translucent" means, for example, to suppress transmission of light having a wavelength that affects imaging by the observation unit. When the observation unit can perform fluorescent observation, the wavelength of the light may be, for example, a wavelength corresponding to the fluorescence to be detected. As a specific example, the non-translucent material can be, for example, the above-mentioned material for forming each region. The size and shape of each region are not particularly limited, and can be determined appropriately depending on the size and shape of a member (unit) placed in each region. In the cell treatment apparatus 200 according to the present embodiment, the first chamber 71 and the second chamber 72 are configured by separate housings, and the housing configuring the first chamber 71 and the housing configuring the second chamber 72 are placed adjacent to each other. The present invention, however, is not limited thereto, and the first chamber 71 and the second chamber 72 may be configured by a single housing and the first chamber 71 and the second chamber 72 may be divided in the single housing. In the cell treatment apparatus 200 according to the present embodiment, the first chamber 71 and the second chamber 72 are configured by separate housings. Thus, for example, each member in the cell treatment apparatus 200 can be maintained easily, and the cell treatment apparatus 200 can be assembled easily. In the present embodiment, the first chamber 71 is a cell treatment chamber 1, that is, the first chamber 71 includes one cell treatment chamber 1. The cell treatment apparatus 200 is not limited thereto and may include two or more cell treatment chambers 1. In this case, each cell treatment chamber 1 is preferably separated in the first chamber 71 by a wall(s) or the like. Preferably, the first chamber 71 is placed above the second chamber 72. When the cell culture vessel 11 is irradiated with lasers by the laser projection unit 4 described below from above, it is required to place an opening 45 in a culture medium inside the cell culture vessel 11 to stabilize the focal position of the laser projection unit 4. However, when the laser irradiation is performed in this state, a problem that the components of the culture medium burn and adhere to the periphery of the opening 45 arises, which causes contamination of the opening 45. Thus, contamination of the emission port for the laser projection unit 4 can be prevented by placing the members as in the cell treatment apparatus 200 according to the present embodiment when the cells in the cell culture vessel 11 are treated by the laser projection unit 4 to be described below, for example. Therefore, the cell treatment apparatus 200 according to the present invention can stabilize the output of the laser emitted from the laser projection unit 4 and can efficiently treat cells, for example.

Next, as shown in FIG. 7, the cell treatment apparatus 200 according to the present embodiment includes an observation unit including the cell culture vessel placement unit 12, the observation unit 2, the light source moving unit 31, the laser projection unit 4, the laser moving unit 51, and the control unit 6 as main components, and the laser projection unit 4 as main components. The configuration of the observation unit 2 except for the laser projection unit 4 and the light source 26 in the cell treatment apparatus 200 according to the present embodiment is the same as that of the cell treatment apparatus 100 according to the first embodiment, and reference can be made to the description as to the cell treatment apparatus 100. In FIG. 7, the outer wall of the double wall of the first chamber 71 to be described below is not shown. In the cell treatment apparatus 200 according to the present embodiment, the observation unit 2 includes the light source 26. The light source moving unit 31, which is the observation moving unit, includes an XY stage 31a and an arm 31b. The laser moving unit 51 includes an XY stage 51b and carriages 51a and 51c. The light source 26 and the light source moving unit 31 are placed in the first chamber 71 (cell treatment chamber 1). The light source 26 is movable by the light source moving unit 31. In the second chamber 72, the observation unit 2, the laser projection unit 4, and the laser moving unit 51 are placed. The observation unit 2 and laser projection unit 4 are movable by the laser moving unit 51. In the third chamber 73, the control unit 6 and a power supply unit 27 are placed. The cell culture vessel placement unit 12 is formed as a part of a partition wall between the first chamber 71 and the second chamber 72. The cell culture vessel 11 is placed in the cell culture vessel placement unit 12. While the cell treatment apparatus 200 according to the present embodiment includes the cell culture vessel 11, the cell culture vessel placement unit 12, the light source 26, the light source moving unit 31, the laser moving unit 51, the second chamber 72, and the third chamber 73, these members are optional, and the cell treatment apparatus 200 may or may not include them. The cell treatment apparatus 200 according to the present embodiment may not include the first chamber 71 (cell treatment chamber 1).

The first chamber 71 includes a work opening 211a on its front (frontward in FIG. 6) and a maintenance opening 211b for maintenance on its side. The opening 211a is a work opening for working on treatment of an object to be observed in the cell treatment chamber 1 as the first chamber 71. The opening 211b is a maintenance opening through which the cell treatment chamber 1 can be maintained. The area of the opening 211a is preferably smaller than that of the opening 211b so that the maintenance operation is facilitated, for example. The size and number of the openings 211a and 211b are not particularly limited, and reference can be made, for example, to the size and number of the work openings and the maintenance openings in the safety cabinet. As a specific example, regarding the size and number of the openings 211a and 211b, reference can be made, for example, to the safety cabinet standard specified in EN12469:2000, which is the EN standard. The number of the openings 211b is not particularly limited and any number of openings 211b can be provided. Preferably, two or more openings 211b are provided so that maintenance becomes easier, for example. The locations of the opening 211a and the opening 211b in the first chamber 71 are not particularly limited and the opening 211a and the opening 211b can be provided any location. Preferably, the opening 211a and the opening 211b are placed at different locations (for example, at different side surfaces) of the first chamber 71. While the opening 211b is primarily intended to facilitate maintenance in the cell treatment apparatus 200 in the present embodiment, the opening 211b may be used for other purposes. The cell treatment apparatus 200 according to the present embodiment, for example, enables observation of movement and the like of each of inside members through the opening 211b, thereby allowing direct observation of a defect site when a problem occurs in the cell treatment apparatus 200. Thus, the problem can be handled appropriately.

The front wall of the first chamber 71 is a double wall having an outer wall and an inner wall, and a door 212a opens and closes the opening 211a by raising and lowering a rail placed in the space between the outer wall and the inner wall. The opening 211b can be opened and closed by detaching and attaching the door 212b covering the opening 211b. For example, when cells are treated in the cell treatment chamber 1, the opening 211b is preferably sealed with the door 212b. Thus, for example, the gas outside the cell treatment apparatus 200 and the dust contained in the gas can be prevented from flowing into the cell treatment chamber 1. In the cell treatment apparatus 200 according to the present embodiment, the opening 211a and the door 212a thereof, and the opening 211b and the door 212b thereof are optional, the cell treatment apparatus 200 may or may not include them, and may include only either of the openings and the doors. The wall of the first chamber 71 may a double door or a single door, and the former is preferable because the size of the cell treatment apparatus 200 can be reduced by placing other members inside the double wall in the first chamber 71. When the wall of the first chamber 71 is a single wall, the door 212a is placed outside the first chamber 71, for example, like the door 212b. The type of opening and closing of the door is not particularly limited, and may be, for example, a lifting type such as the door 212a, an external type such as the door 212b, or other types. Examples of the other type include a double-door type, an accordion type, a pull door type, and the like. The material for forming the door is not particularly limited, and, for example, the above-mentioned material for forming each region can be used, and a non-translucent material is preferable.

As shown in FIG. 8, the inside of the first chamber 71 of the cell treatment apparatus 200 according to the present embodiment is a cell treatment chamber 1 for treating an object to be observed and can be closed by closing the doors 212a and 212b, that is, is openable and closable. The cell treatment chamber 1 includes: a light source moving unit 31 having an XY stage 31a and an arm 31b; a suction/discharge unit 213; a light source 26; a drainage container placement portion 214a; a storage container placement portion 215a; a cell culture vessel placement unit 12; and a collection container placement portion 216a. While the cell treatment chamber 1 includes the light source moving unit 31 including the XY stage 31a and the arm 31b, the suction/discharge unit 213, the drainage container placement portion 214a, the storage container placement portion 215a, and the collection container placement portion 216a in the present embodiment, these members are optional and the cell treatment chamber 1 may or may not include any one or more of them. The XY stage 31a is placed on the bottom surface of the cell treatment chamber 1 and is placed so as to be movable in the X-axis direction and the Y-axis direction. The arm 31b having a pair of arms is placed on the XY stage 31a. At the end of one of the arms in the arm 31b, the suction/discharge unit 213 is placed with its suction/discharge port face downward. Further, at the end of the other arm in the arm 31b, the light source 26 is placed so as to be able to emit illumination light toward the cells 13. The drainage container placement portion 214a, the storage container placement portion 215a, the cell culture vessel placement unit 12, and the collection container placement portion 216a are placed on the bottom surface of the cell treatment chamber 1 in this order along the moving direction of the XY stage 31a in the X-axis direction. A drainage container 214b including a tip member detachment unit 214c is placed in the drainage container placement portion 214a, a storage container 215b is placed in the storage container placement portion 215a, and a collection container 216b is placed in the collection container placement portion 216a.

Regarding the light source moving unit 31, for example, reference can be made to the description as to the observation moving unit 3 in the cell treatment apparatus 100 according to the first embodiment. While the cell treatment apparatus 200 according to the present embodiment can move the light source 26 and the suction/discharge unit 213 by the XY stage 31a and the arm 31b that are collectively the light source moving unit 31, the suction/discharge unit 213 may be moved by a drive unit other than the light source moving unit 31. In this case, the moving direction of the drive unit that can move the suction/discharge unit 213 is not particularly limited, and is, for example, any one direction, two directions, or all directions of the X-axis direction, the Y-axis direction, and the Z-axis direction. In the present embodiment, the XY stage 31a is a known stage that can move an object at high speed and accurately along the X-axis direction and the Y-axis direction through a linear motor carriage or the like, for example. While the arm 31b is extendable in the vertical direction (Z-axis direction), the arm 31b may be fixed. In the latter case, the light source moving unit 31 can move the suction/discharge unit 213 only on the XY plane, that is, only in the X-axis direction and the Y-axis direction in FIG. 8.

The suction/discharge unit 213 sucks and discharges, for example, the culture medium, the cells 13, the target cells 13a, the non-target cells 13b, and the like in the cell culture vessel 11. The suction/discharge unit 213 is used, for example, by mounting a tip member to be described below on its suction/discharge port side. The suction/discharge unit 213 is not particularly limited, and, for example, a known suction/discharge unit can be used. Specific examples thereof include an electric pipettor and an electric syringe pump.

The drainage container placement portion 214a is a region where a drainage container 214b for draining a liquid sucked by the suction/discharge unit 213 can be placed. While the drainage container 214b is placed in the drainage container placement portion 214a in the present embodiment, the drainage container 214b is optional, and may or may not be included. In the present embodiment, the drainage container 214b is a box having an upper opening, and a wall on the storage container placement portion 215a side, extending upward. The wall extending upward, includes a wall (upper surface) substantially parallel to the bottom surface of the cell treatment chamber 1, including the tip member detachment unit 214c formed as a semicircular recess (notch) at the upper end thereof. The drainage container 214b can collect a tip member detached from the suction/discharge unit 213. Thus, for example, the drainage container 214b can also be referred to as a tip member collection container, and the drainage container placement portion 214a can also be referred to as a tip member collection container placement portion. While the tip member detachment unit 214c is formed in the drainage container 214b, these members may be placed separately. The tip member detachment unit 214c may be placed in the vicinity of the suction/discharge unit 213, specifically in the arm 31b of the light source moving unit 31 in which the suction/discharge unit 213 is placed.

The storage container placement portion 215a is an area in which the storage container 215b storing the tip member detachable from the suction/discharge unit 213 can be placed. While the storage container 215b is placed in the storage container placement portion 215a in the present embodiment, the storage container 215b is optional, and may or may not be included. The tip member is not particularly limited, and may be any member as long as it can store the liquid sucked by the suction/discharge unit 213 therein. For example, when the suction/discharge unit 213 is a pipettor, a tip member may be a chip. The storage container 215b may be, for example, a rack in which the chip is stored. The cell treatment apparatus 200 according to the present embodiment includes the tip member detachment unit 214c and the storage container placement portion 215a, and thus the movement of the members at the time of sucking and discharging the medium, the cells, and the like in the cell culture vessel 11 can be simplified (shortened).

The collection container placement portion 216a is a region where a collection container 216b for collecting a suction liquid containing the cells collected by the suction/discharge unit 213 can be placed. While the collection container 216b is placed in the collection container placement portion 216a in the present embodiment, the collection container 216b is optional, and may or may not be included. Examples of the collection container 216b include culture vessels such as known dishes and known flasks.

In the present embodiment, on the bottom surface of the cell treatment chamber 1, the drainage container placement portion 214a, the storage container placement portion 215a, the cell culture vessel placement unit 12, and the collection container placement portion 216a are disposed in this order on the plane on which the cell culture vessel placement unit 12 is placed, i.e., the XY plane along the direction of movement of the XY stage 31a in the long axis direction (X-axis direction). However, these placement portions may not be placed along the long axis direction, and may not be placed in this order. In the present embodiment, the drainage container placement portion 214a, the storage container placement portion 215a, the cell culture vessel placement unit 12, and the collection container placement portion 216a are placed in the above-mentioned order. Thus, for example, the suction/discharge unit 213 can move linearly, and the movement of the members at the time of sucking and discharging the medium, the cells, and the like in the cell culture vessel 11 can be simplified (shortened).

As shown in FIG. 9, a camera 217, illumination lamps 218a and 218b, and a germicidal lamp 219 are provided above the opening 211a in the front wall of the cell treatment chamber 1 in the cell treatment apparatus 200 according to the present embodiment. The illumination lamps 218a and 218b are placed on both sides of the camera 217 in the X-axis direction, and the germicidal lamp 219 is placed above the camera 217.

While the camera 217 is provided as the imaging device of the first chamber 71 in the present embodiment, the imaging device of the first chamber 71 is optional, and may or may not be included. The imaging device of the first chamber 71 is not limited to a camera and is only required to be able to image the inside of the first chamber 71, i.e., the cell treatment chamber 1. The imaging device of the first chamber 71 is not particularly limited, and a known imaging device such as a microscope or a camera can be used, and a combination of the known imaging device and a solid-state imaging element (image sensor) such as a CCD or a Complementary MOS (CMOS) can be used. While the camera 217 is placed in the front wall of the cell treatment chamber 1, the position of the camera 217 is not particularly limited, and the camera 217 may be placed at any position and preferably placed to allow imaging a wide range within the cell treatment chamber 1. Specifically, in the case where the XY stage 31a and the arm 31b which are collectively the light source moving unit 31 and the suction/discharge unit 213 are placed in back (the upper left side in FIG. 8) of the cell culture vessel placement unit 12 in the cell treatment chamber 1 as in the cell treatment apparatus 200 according to the present embodiment, it is preferable to place the camera 217 in front (the lower right side in FIG. 8) of the cell treatment chamber 1 so that an image of a wide range within the cell treatment chamber 1 can be taken. It is preferable that the first imaging device can take an image at multiple magnifications (for example, different magnifications). However, the first imaging device may be able to take an image at one magnification. The magnification means, for example, an imaging magnification. As a specific example, the camera 217 includes lenses with multiple magnifications (for example, different magnifications). The imaging device of the first chamber 71 may be able to perform optical zooming, digital zooming, or the like, for example. The cell treatment apparatus 200 according to the present embodiment includes a camera 217. Thus, for example, the operation inside the cell treatment chamber 1 can be checked, and the reliability of the operation can be improved. The number of the imaging devices of the first chamber 71 placed inside the cell treatment chamber 1 is not particularly limited, and may be one or more.

While the illumination lamps 218a and 218b are provided as the illumination unit in in the present embodiment, the illumination unit is optional, and may or may not be included. The illumination unit is not limited to the illumination lamp and is only required to be able to project light (illuminating) into the cell treatment chamber 1. The illumination unit is not particularly limited, and, for example, a known illumination such as a fluorescent lamp or a LED lamp can be used. While the illumination lamps 218a and 218b are placed in the front wall inside the cell treatment chamber 1 in the present embodiment, the positions of the illumination lamps 218a and 218b are not particularly limited and the illumination lamps 218a and 218b can be placed at any positions. Preferably, the illumination lamps 218a and 218b are placed such that they can be project light onto a wide area within the cell treatment chamber 1, i.e., they are less prone to throw shadows in the cell treatment chamber 1. Specifically, in the case where the XY stage 31a and the arm 31b which are collectively the light source moving unit 31 and the suction/discharge unit 213 are placed in back (the upper left side in FIG. 8) of the cell culture vessel placement unit 12 in the cell treatment chamber 1 as in the cell treatment apparatus 200 according to the present embodiment, it is preferable to place the illumination lamps 218a and 218b in front (the lower right side in FIG. 8) of the cell treatment chamber 1 so that light can be projected onto a wide range within the cell treatment chamber 1. The cell treatment apparatus 200 according to the present embodiment includes the illumination lamps 218a and 218b. Thus, for example, the operation inside the cell treatment chamber 1 can be checked, and the reliability of the operation can be improved. The number of the illumination units placed inside the cell treatment chamber 1 is not particularly limited, and may be one or more.

While a germicidal lamp 219 is provided as a germicidal unit in the present embodiment, the germicidal unit is optional, and may or may not be included. Moreover, the germicidal unit is not limited to the germicidal lamp and is only required to be able to disinfect the inside of the cell treatment chamber 1, specifically, the periphery of the cell culture vessel placement unit 12. The germicidal unit is not particularly limited, and for example, a known germicidal unit such as a germicidal lamp, an ultraviolet LED lamp, or the like can be used. While the germicidal lamp 219 is placed in the front wall inside the cell treatment chamber 1 in the present embodiment, the position of the germicidal lamp 219 is not particularly limited, and the germicidal lamp 219 may be placed at any position. For example, dust and the like outside the cell treatment apparatus 200 enter through the openings 211a and 211b. It is thus preferable that the germicidal lamp 219 is placed so as to be able to disinfect the vicinities of the openings 211a and 211b. Specifically, in the case where the opening 211a is provided in the front wall of the cell treatment chamber 1 as in the cell treatment apparatus 200 according to the present embodiment, the germicidal unit is preferably placed above the opening 211a in the front wall of the cell treatment chamber 1. In the case where an opening 211b is provided in the wall on the side surface side of the cell treatment chamber 1 as in the cell treatment apparatus 200 according to the present embodiment, the germicidal unit is preferably placed above the opening 211b in the wall on the side surface side of the cell treatment chamber 1. When the cell treatment apparatus 200 includes the illumination unit and the germicidal unit, both of them are preferably placed on the same wall of the cell treatment chamber 1, for example, on a wall in which the opening 211a is provided. In this case, the germicidal unit is provided preferably above the illumination unit. The cell treatment apparatus 200 according to the present embodiment includes a germicidal lamp 219. Thus, for example, the cleanliness of the inside of the cell treatment chamber 1 is improved. The number of germicidal units placed in the cell treatment chamber 1 is not particularly limited, and may be one or more.

In the present embodiment, as to the size, shape, structure, and the like of the cell treatment chamber 1, which is the first chamber 71, reference can be made to those of the safety cabinet, for example, and as a specific example, reference can be made to the safety cabinet standard specified in EN12469:2000.

As shown in FIGS. 10A and 10B, the cell culture vessel placement unit 12 in the cell treatment apparatus 200 according to the present embodiment includes an upper lid 121 and a bottom 122, and the upper lid 121 is detachably attached to the bottom 122. In the present embodiment, the cell culture vessel placement unit 12 is a box including the upper lid 121 and the bottom 122, and cell culture vessel 11 is placed inside the box. However, the cell culture vessel placement unit 12 is not limited thereto as long as the following is satisfied: the cell culture vessels 11 can be placed in the cell culture vessel placement unit 12, the cell culture vessel placement unit 12 is placed so as to be adjacent to the second chamber 72 in the cell treatment chamber 1, and the adjacent portion (bottom plate 125 in FIGS. 10A and 10B) of the cell culture vessel placement unit 12 to the second chamber 72 is translucent. The "translucent" means, for example, transmitting of the laser light such as a laser image projected from the laser projection unit 4 in the second chamber 72. A translucent region 123 is provided in the upper lid 121 so that the cell culture vessel 11 can be irradiated with light from the light source 26. The translucent region 123 is, for example, a region through which illumination light irradiated from the light source 26 is transmitted. The translucent region 123 is formed of, for example, a transparent glass plate, an acrylic plate, or the like. The bottom 122 includes a bottom wall 124 and a translucent bottom plate 125. The translucent bottom plate 125 is formed of, for example, a transparent glass plate, an acrylic plate, or the like. The bottom plate 125 is adjacent to the second chamber 72. For this reason, it can also be said that the adjacent portion of the cell culture vessel placement unit 12 to the second chamber 72, i.e., the bottom plate 125 forms a part of the wall of the cell treatment chamber 1. The contact portion between the bottom plate 125 and the wall of the cell treatment chamber 1 is preferably sealed by a sealing compound such as a packing, a sealing member, or the like, for example. As a result, for example, the gas in the second chamber 72 and dust contained in the gas can be prevented from flowing into the cell culture vessel placement unit 12 and the cell treatment chamber 1. The bottom wall 124 includes four recesses 126 in which four cell culture vessels 11 can be respectively placed, and the side surface of each recess 126 has a reversely tapered shape that narrows from the inside of the cell treatment chamber 1 toward the outside of the cell treatment chamber 1 (from top toward bottom in FIG. 10B). Each recess 126 includes a projection 127 projecting toward the inside of the recess 126 on the end side of the bottom plate 125. The bottom end of the cell culture vessel 11 is in contact with the projection 127. In the cell treatment apparatus 200 according to the present embodiment, the bottom wall 124 has four recesses 126. However, the number of the recesses 126 in the bottom wall 124 is not limited thereto, and can be appropriately determined according to the number of the cell culture vessels 11 to be placed. The size of each recess 126 can be appropriately determined depending on the size of the cell culture vessel 11 to be placed. In the cell culture vessel placement unit 12 according to the present embodiment, the recess 126 has the above-described structure. Thus, for example, the cell culture vessel 11 can be placed in the cell culture vessel placement unit 12 regardless of the shape of the side surface of the cell culture vessel 11. In the cell treatment apparatus 200 according to the present embodiment, the bottom wall 124 is integrally formed with the wall of the bottom surface and the wall of the side surface. However, the bottom wall 124 is not limited thereto, and the wall of the bottom surface and the wall of the side surface may be different members. When the wall of the bottom surface and the wall of the side surface in the bottom wall 124 are configured by different members, for example, multiple walls of the bottom surfaces for the bottom wall 124, having different numbers and sizes of recesses 126 can be provided in advance. Thus, for example, the member of the wall of the bottom surface for the bottom wall 124 can be replaced with a member having a suitable number of recesses with suitable sizes for placement of the cell culture vessels 11 depending on the size and number of the cell culture vessels 11. Therefore, the cell culture vessels 11 can be suitably placed.

As shown in FIGS. 11 and 12, in the cell treatment apparatus 200 according to the present embodiment, the circulator 24 includes an intake portion 24a, circulation path 24b, a gas supply portion 24c, and a discharge portion 24d. Thus, the circulator 24 circulates the gas in the cell treatment chamber 1.

The intake portion 24a intakes the gas in the cell treatment chamber 1. The intake portion 24a may intake gas outside the cell treatment apparatus 200 instead of or in addition to the gas in the cell treatment chamber 1. In the present embodiment, the intake portion 24a is placed in the vicinity of (e.g., directly below) the opening 211a of the cell treatment chamber 1. Specifically, the intake portion 24a has multiple openings (e.g., slits) formed on its upper surface (not shown) and is placed below the opening 211a such that the openings communicate with the opening 211a. By placing the intake portion 24a in the vicinity of the opening 211a of the cell treatment chamber 1 as described above, for example, the gas outside the cell treatment apparatus 200 and the dust and the like contained in the gas can be prevented from flowing into the cell treatment chamber 1 at the time when the operator opens the door 212a and works in the cell treatment chamber 1. The intake portion 24a may be placed in the vicinity of the opening 211b instead of or in addition to the opening 211a. The intake portion 24a may intake the gas in the cell treatment chamber 1 with a blowing unit such as a fan, for example.

The circulation path 24b connects the intake portion 24a with the gas supply portion 24c and the discharge portion 24d. In the present embodiment, the circulation path 24b is placed in a space between the outer wall and the inner wall and above the first chamber 71. The circulation path 24b is, for example, a hollow tube. One end of the circulation path 24b communicates with the intake portion 24a, and the other end communicates with the gas supply portion 24c and the discharge portion 24d. When the circulation path 24b is placed in a space between the outer wall and the inner wall as in the cell treatment apparatus 200 according to the present embodiment, for example, the size of the cell treatment apparatus 200 can be reduced. While the circulator 24 includes the circulation path 24b in the present embodiment, the circulation path 24b may or may not be included. In the latter case, the intake portion 24a is connected to, for example, directly the gas supply portion 24c and the discharge portion 24d. The circulation path 24b may blow the gas taken in by the intake portion 24a to the gas supply portion 24c and the discharge portion 24d by a blowing unit such as a fan, for example.

When the circulation path 24b includes the blowing unit, the blowing unit may be placed in the vicinity of the intake portion 24a, the gas supply portion 24c, or the discharge portion 24d, or may be placed in any other positions such as the central portion thereof. It is preferable to place the blowing unit in the vicinity of the intake portion 24a, because the intake from the intake portion 24a is improved, and the dust and the like can be effectively prevented from flowing into the cell treatment chamber 1, for example, as compared with the downflow generated by the gas supply portion 24c to be described below. When the blowing unit is placed in the vicinity of the intake portion 24a, it is preferable that the blowing unit be placed in, for example, the second chamber 72 or the third chamber 73. As a specific example, when the circulation path 24b further includes the blowing unit in the cell treatment apparatus 200 according to the present embodiment, the blowing unit is placed in front (the lower left side in FIG. 6), that is, on the lower side of the intake portion 24a in the second chamber 72 or the third chamber 73. In this case, the circulation path 24b connects the intake portion 24a with the intake side of the blowing unit and connects the blowing side of the blowing unit with the gas supply portion 24c and the discharge portion 24d. That is, the circulation path 24b is placed in the second chamber 72 or the second chamber 72 and the third chamber 73, the space between the outer wall and the inner wall, and above the first chamber 71.

The gas supply portion 24c supplies a part of the gas taken in by the intake portion 24a into the cell treatment chamber 1. In the present embodiment, the gas supply portion 24c communicates with the upper end of the first chamber 71 such that the gas taken in by the intake portion 24a can be supplied into the cell treatment chamber 1. The gas supply portion 24c may supply the gas into the cell treatment chamber 1 by the blowing unit such as a fan, for example. The gas supply portion 24c may include, for example, a gas purification unit. In this case, the gas supplied from the gas supply portion 24c into the cell treatment chamber 1 passes through the gas purification unit. When the gas supply portion 24c includes the gas purification unit, for example, the dust or the like can be prevented from flowing into the cell treatment chamber 1. Examples of the gas purification unit include filters for collecting fine particulates such as a high efficiency particulate air filter (HEPA filter), an ultra-low penetration air filter (ULPA filter), and the like. In the cell treatment apparatus 200 according to the present embodiment, the upper part of the cell treatment chamber 1 is connected to the gas supply portion 24c. Thus, for example, blowing air from the gas supply portion 24c causes downflow, which can more effectively prevent dust and the like from flowing into the cell treatment chamber 1 from the opening 211a.

The discharge portion 24d discharges the remainder of the gas taken in by the intake portion 24a to the outside of the cell treatment chamber 1, specifically, to the outside of the cell treatment apparatus 200. In the present embodiment, the discharge portion 24d is placed at an upper end (topmost portion) of the cell treatment apparatus 200 such that the gas taken in by the intake portion 24a can be discharged to the outside of the cell treatment apparatus 200. When the discharge portion 24d is provided in the topmost portion of the cell treatment apparatus 200 in this manner, for example, the size of the cell treatment apparatus 200 can be reduced, and the dust stirred up due to discharge can be prevented from flowing into the cell treatment chamber 1. The discharge portion 24d may discharge the gas to the outside of the cell treatment apparatus 200 with a blowing unit such as a fan, for example. The discharge portion 24d may include, for example, a gas purification unit. In this case, the gas discharged from the discharge portion 24d to the outside of the cell treatment apparatus 200 passes through the gas purification unit. When the discharge portion 24d includes a gas purification unit, for example, fine particles or the like generated in the cell treatment chamber 1 can be prevented from blowing out of the cell treatment apparatus 200.

In the circulator 24, as to the size, shape, structure, and the like of each portion, reference can be made to those of the safety cabinet, for example, and as a specific example, reference can be made to the safety cabinet standard specified in EN12469:2000.

As shown in FIG. 13A, in the cell treatment apparatus 200 according to the present embodiment, the second chamber 72 includes the observation unit 2, the laser projection unit 4, and the laser moving unit 51. While the cell treatment apparatus 200 according to the present embodiment includes the laser moving unit 51, the laser moving unit 51 is optional as described above, and the cell treatment apparatus 200 may or may not include the laser moving unit 51. The laser moving unit 51 includes an XY stage 51b and carriages 51a and 51c. The XY stage 51b is placed on the plane on which the cell culture vessel placement unit 12 is placed, i.e., on the bottom surface of the second chamber 72 substantially parallel to the XY plane. On a common rail (moving path) in the Y-axis direction in the XY stage 51b, two rails in the X-axis direction are placed so as to be movable on the common rail. The carriages 51a and 51c are placed on the two rails, respectively, in the X-axis direction so as to be movable on the respective rails. Above the XY stage 51b, the laser projection unit 4 is placed on the carriage 51a such that the opening 45 face upward (Z-axis direction) so as to be able to project the laser image onto the cells 13. Furthermore, above the XY stage 51b, the observation unit 2 is placed on the carriage 51c so that the objective lenses 21a, 21b, and 21c can observe or image the cells 13 in the cell culture vessel 11. In the cell treatment apparatus 200 according to the present embodiment, the carriages 51a and 51c may be configured to be able to move up and down in the vertical direction (Z-axis direction), for example.

In the cell treatment apparatus 200 according to the present embodiment, the observation unit 2 and the laser projection unit 4 can be moved by the XY stage 51b which is the laser moving unit 51. Therefore, it can be said that the laser moving unit 51 in the cell treatment apparatus 200 according to the present embodiment also serves as the observation moving unit 3 in the cell treatment apparatus 100 according to the first embodiment. The movement of the observation unit 2, however, is not limited thereto, and the observation unit 2 may be moved by a drive unit other than the laser moving unit 51. The drive unit may be, for example, the observation moving unit 3 in the cell treatment apparatus 100 according to the first embodiment. While the laser moving unit 51 in the present embodiment also serves as the observation moving unit 3 in the cell treatment apparatus 100 according to the first embodiment, the observation moving unit and the laser moving unit 51 may be configured independently. As a specific example, as shown in FIG. 13B, the observation moving unit 32 and the laser moving unit 51 may be placed on the bottom surface of the second chamber 72. The observation moving unit 32 includes a carriage 32a and an XY stage 32b. The laser moving unit 51 includes the carriage 51a and the XY stage 51*b*. The moving directions of the observation moving unit 32 and the laser moving unit 51 are not particularly limited, and are, for example, any one direction, two directions, or all directions of the X-axis direction, the Y-axis direction, and the Z-axis direction. When the laser moving unit 51 can move the laser projection unit 4, for example, substantially orthogonal to the plane on which the cell culture vessel placement unit 12 is placed, i.e., the bottom surface of the cell culture vessel 11, the laser moving unit 51 can adjust the laser image size to be described below. In this case, the laser moving unit 51 also serves as an image-size adjusting unit to be described below, for example. In the present embodiment, the XY stage 32*b* and 51*b* are known stages that can move an object at high speed and accurately along the X-axis direction and the Y-axis direction through a linear motor carriage or the like, for example.

It is preferable that the observation moving unit and the laser moving unit 51 can move the observation unit 2 and the laser projection unit 4 in the first direction (for example, the direction indicated by the arrow Yin FIG. 13A) in a plane substantially parallel to the plane on which the cell culture vessel placement unit 12 is placed as in the XY stage 51*b* of the present embodiment, and that the movement of the observation unit 2 in the first direction by the observation moving unit and the movement of the laser projection unit 4 in the first direction by the laser moving unit 51 are on the same straight line. As described above, by moving the observation unit 2 and the laser projection unit 4 on the same straight line, for example, when performing cell treatment such as treating the cells 13 in the cell culture vessel 11 by the laser projection unit 4 after being imaged by the observation unit 2, the number of times of moving each unit can be reduced, and the treatment time can be reduced. Further, as in the XY stage 51*b* of the present embodiment, it is preferable that the observation moving unit include the carriage 51*c* on which the observation unit 2 is placed and a moving path (rail) placed along the first direction and along which the carriage 51*c* moves, and that the laser moving unit 51 includes the carriage 51*a* on which the laser projection unit 4 is to be placed and a moving path (rail) placed along the first direction and along which the carriage 51*a* moves, wherein the moving path of the observation unit 2 and the moving path of the laser projection unit 4 are the same. Such a configuration allows a reduction in the number of times of moving each unit when performing cell treatment such as treating the cells 13 in the cell culture vessel 11 by the laser projection unit 4 after being imaged by the observation unit 2, and further reduce the treatment time.

In the cell treatment apparatus 200 according to the present embodiment, the observation unit 2 includes the objective lenses 21*a*, 21*b*, and 21*c* having three different magnifications. The present invention, however, is not limited thereto, and the observation unit 2 may not include an objective lens, or may include one or more types of objective lenses 21. When the observation unit 2 includes a plurality of objective lenses 21, the magnifications of the plurality of objective lenses 21 are preferably different magnifications, such as, for example, 2×, 4×, and 8×, respectively. In the case of including the observation unit 2 that includes the imaging device (camera 217) of the first chamber 71 and the objective lens 21 as in the cell treatment apparatus 200 according to the present embodiment, it is preferable that the magnification of the objective lens 21 of the observation unit 2 be higher than the magnification of the imaging device of the first chamber 71 so that the cells in the cell culture vessel 11 can be imaged more clearly.

The laser moving unit 51 may move the laser projection unit 4 in the vertical direction (the direction indicated by the arrow Z in FIGS. 13A and 13B). In the case of moving the laser projection unit 4 vertically, it is preferable to move the laser projection unit 4 such that the component of the laser projection unit 4 closest to the cell treatment chamber 1 does not come into contact with the bottom surface of the cell treatment chamber 1, preferably the bottom surface of the cell culture vessel placement unit 12. As a specific example, it is preferable that the laser moving unit 51 moves the laser projection unit 4 such that the component of the laser projection unit 4 closest to the cell treatment chamber 1 does not approach within 1 mm with reference to the bottom surface of the cell culture vessel placement unit 12. When the laser moving unit 51 moves the component of the laser projection unit 4 closest to the cell treatment chamber 1 in such a range, for example, it is possible to prevent swaying of the culture medium in the cell culture vessel 11 placed in the cell culture vessel placement unit 12, which is caused by contact between the component of the laser projection unit 4 closest to the cell treatment chamber 1 and the bottom surface of the cell culture vessel placement unit 12.

In the present embodiment, the laser projection unit 4 is placed in front (the lower left side in FIGS. 13A and 13B), and the observation unit 2 is placed in back (the upper right side in FIGS. 13A and 13B). The positional relationship between the laser projection unit 4 and the observation unit 2, however, is not limited thereto, and for example, the laser projection unit 4 may be placed in back and the observation unit 2 may be placed in front. Generally, the volume of the observation unit 2 is larger than that of the laser projection unit 4. Thus, in the case where the cell culture vessel placement unit 12 is placed in front in the first chamber 71, the size of the cell treatment apparatus 200 can be reduced by placing the observation unit 2 in back and placing the laser projection unit 4 in front.

The cell treatment apparatus 200 according to the present embodiment may further include a laser image adjusting unit that adjusts the size of the laser image projected onto a projected object such as the cells 13 or the bottom surface of the cell culture vessel 11. The size of the laser image means, for example, the area of the laser image at the contact portion between the laser image projected by the laser projection unit 4 and the projected object. The size of the laser image can be adjusted, for example, by switching the lens system of the laser projection unit 4, or by changing the distance between the laser projection unit 4 and the projected object. In the former case, it is preferable that the laser projection unit 4 include, for example, a plurality of lenses, and that the laser image adjusting unit adjust the size of the laser image by changing the lenses. The lens may be changed manually, for example, or may be changed by the control unit 6 to be described below. In the latter case, for example, the cell treatment apparatus 200 further includes a lens changing unit, and the lens changing unit changes the lenses. Further, when the laser image adjusting unit changes the distance, it is preferable that the laser image adjusting unit adjust the size of the laser image by adjusting the distance between the laser projection unit 4 and the projected object. The distance between the laser projection unit 4 and the projected object means, for example, a distance in the direction substantially orthogonal to the plane on which the cell culture vessel placement unit 12 is placed, i.e., the bottom surface of the cell culture vessel 11. Specifically, the distance between the laser projection unit 4 and the projected object means, for example, the distance between the projected object and the component of the laser projection unit 4 closest to the projected object. The distances between the laser projection unit 4 and the projected object can be adjusted by, for example, the laser moving unit 51. As a specific example, by moving the laser projection unit 4 by the laser moving unit 51 in the direction indicated by the arrow Z, the distance between the laser projection unit 4 and the cells 13 or the bottom surface of the cell culture vessel 11 as the projected object can be adjusted.

When the cell treatment apparatus 200 according to the present embodiment includes the laser image adjusting unit, it is preferable that the control unit 6 described below control the adjustment of the size of the laser image with the laser image adjusting unit.

In the cell treatment apparatus 200 according to the present embodiment, it is preferable that the gas is prevented from moving between the cell treatment chamber 1 and the second chamber 72. The gas can be prevented from moving, for example, by sealing the adjacent portion of the cell treatment chamber 1 to the second chamber 72 with a sealing compound such as a packing, a sealing member, or the like. By preventing the gas from moving in this manner, for example, the inflow of dust contained in the gas into the cell treatment chamber 1 can be prevented.

In the cell treatment apparatus 200 according to the present embodiment, the third chamber 73 includes the control unit 6 and the power supply unit 27. As shown in FIG. 14, in the control unit 6 of the present embodiment, the I/O interface 65 is a device that can communicate with and control the members such as the observation unit 2, the laser image generation portion 42, the laser moving unit 51, the light source moving unit 31, the camera 217, the suction/discharge unit 213, and the light source 26. Except for this point, the control unit 6 of the present embodiment has the same configuration as the control unit 6 of the embodiment, and reference can be made to the description thereof.

In the cell treatment apparatus 200 according to the present embodiment, the control unit 6 has the functions of controlling the observation unit 2, the laser image generation portion 42, the laser moving unit 51, the light source moving unit 31, the camera 217, the suction/discharge unit 213, and the light source 26, so that a control unit does not have to be individually provided in each member, whereby the device can be miniaturized. The present invention, however, is not limited thereto. In the cell treatment apparatus, for example, a control unit as the control unit 6 may be provided in each of the observation unit 2, the laser image generation portion 42, the laser moving unit 51, the light source moving unit 31, the camera 217, the suction/discharge unit 213, and the light source 26, and each member may be controlled by the control unit of each member. The cell treatment apparatus of the present invention may include, for example, the control unit 6 and the control units of the respective members to control the members in cooperation.

In the present embodiment, the control unit 6 controls the imaging of the cell treatment chamber 1 by the camera 217, which is the imaging device of the first chamber 71.

In the present embodiment, the control unit 6 controls observation or imaging by the observation unit 2, generation of a laser image by the laser image generation portion 42, movement of the observation unit 2 and the laser projection unit 4 by the XY stage 51b and the carriages 51a and 51c, which are collectively the laser moving unit 51, movement of the light source 26 by the XY stage 31a and the arm 31b, which are collectively the light source movement unit 31, imaging by the camera 217, suction and discharge by the suction/discharge unit 213, and ON/OFF of the light source 26. The present invention, however, is not limited thereto and the control unit 6 is only required to control generation of a laser image by the laser image generation portion 42. The control of other components is optional and the control unit 6 may or may not control any one or more of the other components.

The power supply unit 27 is not particularly limited, and a known power supply can be used. The power supply unit 27 supplies electric power to members (units) activated by electric power, such as the observation unit 2, the light source moving unit 31, the laser projection unit 4, the laser moving unit 51, the suction/discharge unit 213, the circulator 24, the illumination unit, the germicidal unit, the control unit 6, and the like. Thus, the power supply unit 27 is electrically connected to, for example, the members (units) activated by electric power. The power supply unit 27 supplies electric power at a voltage of, for example, 100 V. This enables the cell treatment apparatus 200 to be used even in a general electric power environment, for example. In the cell treatment apparatus 200 according to the present embodiment, the power supply unit 27 is responsible for the entire power supply, so that a power supply unit is not required to be provided individually for each member, whereby the size and weight of the cell treatment apparatus 200 can be reduced, for example. The present invention, however, is not limited thereto, and, for example, a dedicated power supply unit may be provided for at least one of the units.

The cell treatment apparatus 200 according to the present embodiment may further include a communication portion (not shown) in the third chamber 73. The communication portion has a function of transmitting/receiving data to/from an external device such as a personal computer, a mobile communication device, or the like, or a function of connecting to the Internet or the like, for example, by wire or wireless communication. The communication portion may be, for example, an existing communication module or the like. When a communication portion is provided as described above, the cell treatment apparatus 200 can be connected to the outside. Thus, the cell treatment apparatus 200 can be operated from the outside or can receive data from the outside, for example. In addition, data in the cell treatment apparatus 200 can be browsed by, for example, connecting from the outside.

Next, treatment of cells and collection of treated cells using the cell treatment apparatus 200 according to the present embodiment will be described with reference to examples.

First, the germicidal lamp 219 is turned off, and the illumination lamps 218a and 218b are turned on. In addition, the camera 217 is activated by the control unit 6 to start imaging inside of the cell treatment chamber 1. The image of the inside of the cell treatment chamber 1 taken by the camera 217 is output to a display device via, for example, the control unit 6. Further, the circulator 24 is activated to circulate the gas in the cell treatment chamber 1. Thereafter, an operator opens the door 212a of the opening 211a, places the cell culture vessel 11 in the cell culture vessel placement unit 12, and places the collection container 216b in the collection container placement portion 216a. The laser absorbing layer is formed on the bottom surface of the cell culture vessel 11. After the placement, the operator closes the door 212a of the opening 211a.

Next, the control unit 6 controls the XY stage 51b and the carriage 51c to move, thereby moving the observation unit 2 to below the bottom surface of the cell culture vessel 11. Further, the control unit 6 controls the XY stage 31a to move, thereby moving the light source 26 to above the upper surface of the cell culture vessel 11, i.e., to above the cell culture vessel placement unit 12. Then, in the same manner as in the step S1 in the laser image acquisition method of the cell treatment apparatus 100 according to the first embodiment, the observation unit 2 images a part of or the entire cell culture vessel 11. As described above, the observation unit 2 may image the cells 13 in the cell culture vessel 11 by dividing the cell culture vessel 11 into a plurality of sections, and imaging the plurality of sections. The obtained image is, for example, output to the display device via, for example, the control unit 6.

Next, the control unit 6 creates the laser image information based on the image obtained by the observation unit 2 and the observation position information. The creation of the laser image information can be performed in the same manner as in the step S2 in the laser image acquisition method of the cell treatment apparatus 100 according to the first embodiment. Then, the control unit 6 stores the laser image information in the auxiliary storage device 63.

The control unit 6 controls the XY stage 51b and the carriage 51a to move, thereby moving the laser projection unit 4 to below the bottom surface of the cell culture container 11. The control unit 6 acquires the laser position information as the position of the laser projection unit 4. The control unit 6 reads the laser image information associated with the laser position information among the laser image information based on the laser position information. Next, the control unit 6 controls the laser image generation portion 42 to generate the laser image. As a result, the laser projection unit 4 projects the laser image onto the cells 13 to treat the target cells 13a. The control unit 6 may project the laser image from the projection start position of the laser image at one end of the cell culture container 11 to the projection end position of the laser image at the other end of the cell culture container 11 in the same manner as the cell treatment apparatus 100 according to the first embodiment. When the target cells 13a are present, the control unit 6 controls the XY stage 51b and the carriage 51a to move and then controls the laser projection unit 4 to project the laser image in the same manner as described above.

Next, the control unit 6 controls the XY stage 31a to move, thereby moving the suction/discharge unit 213 to above the storage container 215b. The control unit 6 controls the arm 31b to move up and down, thereby attaching a chip, which is the tip member, to the suction/discharge port side of the suction/discharge unit 213. Next, the control unit 6 controls the XY stage 31a to move, thereby moving the suction/discharge unit 213 to above the cell culture vessel 11. At this moment, in the case of collecting the target cells 13a, the suction/discharge unit 213 moves to above the target cells 13a. On the other hand, in the case of collecting the non-target cells 13b, the suction/discharge unit 213 moves to above the non-target cells 13b. The control unit 6 controls the arm 31b to move down, thereby placing the opening of the chip in the vicinity of the cells 13a or cells 13b to be collected. In this state, the control unit 6 controls the suction/discharge unit 213 to suck the cells 13a or cells 13b to be collected together with the surrounding medium into the chip.

Further, the control unit 6 controls the arm 31b to move up and the XY stage 31a to move, thereby moving the suction/discharge unit 213 to above the collection container 216b. Further, the control unit 6 controls the arm 31b to move down, thereby moving the opening of the chip to the inside of the collection container 216b. In this state, the control unit 6 controls the suction/discharge unit 213 to discharge the medium containing the cells 13a or cells 13b in the chip into the collection container 216b.

After discharging the medium, the control unit 6 controls the arm 31b to move up and the XY stage 31a to move, thereby moving the suction/discharge unit 213 to above the drainage container 214b. Further, the control unit 6 controls the arm 31b to move down and the XY stage 31a to move, thereby catching the upper end of the chip by the tip member detachment unit 214c, which is a recess in the upper surface provided in the drainage container 214b. In this state, the control unit 6 controls the arm 31b to move up, thereby detaching the chip from the suction/discharge unit 213.

Then, the operator opens the door 212a of the opening 211a, collects the cell culture vessel 11 from the cell culture vessel placement unit 12, and collects the collection container 216b from the collection container placement portion 216a. In this manner, the cell treatment apparatus 200 can treat the cells 13 and collect the target cells 13a or the non-target cells 13b. It is to be noted that collecting the cells 13a or 13b by the cell treatment apparatus 200 is an optional step, and may or may not be performed.

The cell treatment apparatus 200 according to the present embodiment can easily subject the cells 13 in the cell culture vessel 11 to treatments such as selection and collection, for example. In addition, since the cell treatment apparatus 200 according to the present embodiment treats the cells not by the operator but by the laser projection unit 4, for example, the operation is not affected by the skill level of the operator. Thus, for example, the quality of the cells 13a or 13b obtained after the treatment is stabilized.

Third Embodiment

Figure 16:
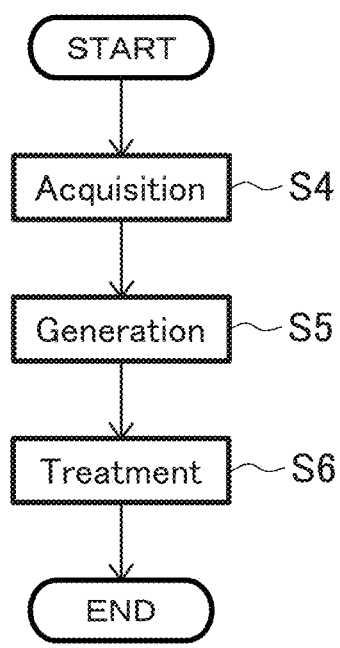
FIG. 16 is a flow chart showing the process of the treatment method according to the third embodiment.

The present embodiment relates to an example of a treatment method. FIG. 16 is a flow chart showing the process of the treatment method according to the present embodiment. As shown in FIG. 16, the treatment method according to the present embodiment includes the step S4 (acquisition), the step S5 (generation), and the step S6 (treatment). The step S4 and the step S5 are optional, and the treatment method may or may not include these steps.

In the acquisition step (S4), an image in the cell culture vessel is acquired. In the acquisition step, for example, an image containing cells in the cell culture vessel may be acquired, an image not including cells in the cell culture vessel may be acquired, or both of them may be acquired. In the acquisition step, for example, an image of a part of or the entire cell culture vessel may be acquired. The image may be an image acquired in advance, or may be an image acquired in the acquisition step. In the former case, the image is stored, for example, in the storage unit, and the image is acquired from the storage unit in the acquisition step. In the latter case, regarding the acquisition step, for example, reference can be made to the description as to the step S1 in the laser image acquisition method of the cell treatment apparatus 100 according to the first embodiment. When an image acquired in the acquisition step is used as the image, the image is acquired by imaging the inside of the cell culture vessel in the acquisition step. In this case, the acquisition step also may be referred to as an imaging step, for example.

In the acquisition step, when the image is acquired by imaging the inside of the cell culture vessel, the image may be acquired by dividing the cell culture vessel into a plurality of sections and imaging the plurality of sections in the acquisition step. In this case, it is preferable to integrate the obtained images of the plurality of sections. When acquiring an image of the entire cell culture vessel, in the acquisition step, it is preferable to divide the entire cell culture vessel into a plurality of sections and image the plurality of sections to image the entire cell culture vessel, thereby acquiring the full image. In this case, in the acquisition step, it is preferable to integrate the obtained images of the respective sections, thereby acquiring the image of the entire cell culture vessel. The method for integrating the images of the respective sections is not particularly limited, and can be a known image processing method.

In the acquisition step, for example, position information may be given to the pixels of the obtained image based on the imaging position in the cell culture vessel. Examples of the positional information include coordinates (two-dimensional coordinates) in the XY axes and coordinates (three-dimensional coordinates) in the XYZ axes.

Next, in the generation step (S5), a laser image to be projected onto the cells is generated based on the image of the inside of the cell culture vessel. Regarding the generation step, for example, reference can be made to the description as to the step S2 in the laser image acquisition method of the cell treatment apparatus 100 according to the first embodiment. In the generation step, the image of the inside of the cell culture vessel for use in the generation of the laser image may be, for example, an image containing cells in the cell culture vessel, an image not containing cells in the cell culture vessel, or both of them. In the generation step, for example, the target cells and the non-target cells are detected in the image of the inside of the cell culture vessel. Then, in the generation step, for example, a laser image defining the presence or absence and/or the intensity of the projection of the laser light is created with the region where the target cells are present as the projection region of the laser light and the region where the non-target cells are present as the non-projection region of the laser light. The method for detecting the target cells and the non-target cells is not particularly limited, and can be performed by a known cell discrimination method. As a specific example, the method for detecting the target cells and the non-target cells may be a method of using a learned model obtained by performing depth learning so as to be able to detect the target cells and the non-target cells. The laser image may be created, for example, by detecting either one of the target cells and the non-target cells. In the generation step, for example, the position information may be given to the pixels of the laser image.

Next, in the treatment step (S6), the laser treatment is performed by projecting the laser image onto the cells in the cell culture vessel. Regarding the treatment step, for example, reference can be made to the description as to the step S3 in the method for treating cells of the cell treatment apparatus 100 according to the first embodiment. The generation step can be performed using, for example, a laser projection apparatus. As the laser projection apparatus, for example, a known apparatus that can project an image of laser light can be used. As a specific example, the laser projection apparatus preferably includes the laser light source and the laser image generation portion that generates a laser image to be projected onto the cells from laser light oscillated from the laser light source. In the treatment step, by using the laser projection apparatus having such a configuration, the laser image can be efficiently projected onto cells in the cell culture vessel, and a variation of the treatment time of the cells 13 can be further suppressed. As a specific example, the laser projection apparatus may be, for example, the cell treatment apparatus of the present invention.

In the treatment step, for example, the laser treatment is performed by projecting the laser images onto a part of or the entire cell culture vessel. In the treatment step, for example, the laser image is projected directly or indirectly onto the cells. When the cell culture vessel includes the laser absorbing layer, it is preferable that the laser image be projected onto the laser absorbing layer in the treatment step.

The treatment method according to the present embodiment may include, for example, a dividing step of dividing the laser image into a plurality of sections. In this case, in the treatment step, laser treatment is performed by projecting the laser images of respective sections onto the cells in the cell culture vessel. The respective sections are not particularly limited, and for example, divided images obtained by dividing the laser image into predetermined widths can be used. When the laser image is divided into the divided images, in the treatment step, laser treatment is performed by projecting the divided images as the laser image onto the cells in the cell culture vessel. In this case, it is preferable that the laser treatment be performed using all the divided images generated by the division in the treatment step. Specifically, the treatment step includes: a first treatment step of projecting the divided image from the projection start position of the divided image at one end of the cell culture vessel to the projection end position of the divided image at the other end of the cell culture vessel; and a second treatment step of projecting the divided image from the projection start position of a new divided image at the other end of the cell culture vessel to the projection end position of the new divided image at one end of the cell culture vessel. The divided image projected in the first treatment step is a divided image different from the divided image projected in the second treatment step. Then, in the treatment step, for example, the first treatment step and the second treatment step are alternately performed until the laser treatment by all divided images is completed. In this case, the treatment step is only required that the first treatment step and the second treatment step as one set is performed one or more sets, and the treatment step may be ended after performing the first treatment step and the second treatment step as one set followed by the first treatment step. Further, when the image of the entire cell culture vessel is acquired in the acquisition step, it is preferable that the first treatment step and the second treatment step be performed repeatedly on the cells of the entire cell culture vessel until the laser treatment is completed in the treatment step, for example.

In this manner, the treatment method of the present embodiment can treat cells in the cell culture vessel.

Since the treatment method according to the present embodiment projects the laser images, different from direct irradiation of laser light which is point-irradiation, the laser light can be irradiated planarly. In the case of direct irradiation of the laser light, if the number of target cells varies greatly, the area to be irradiated with the laser light also varies greatly, and therefore, the irradiation time of the laser light varies greatly. That is, the treatment time varies greatly. On the other hand, when the laser light is irradiated planarly as in the treatment method of the present embodiment, even if the number of the target cells varies greatly, it is only necessary to change the position where the laser light is irradiated (the position where the target cells are present) and the position where the laser light is not irradiated (the position where the non-target cells are present) in the laser image, and the area where the laser image is projected in a single projection does not vary. Thus, according to the treatment method of the present embodiment, it is possible to suppress the variation of the treatment time of treating the cells using the laser light, as compared to the case of direct irradiation of the laser light.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2018-124805 filed on Jun. 29, 2018. The entire subject matter of the Japanese Patent Applications is incorporated herein by reference.

<Supplementary Notes>

A part of or the whole of the above-described embodiments and examples can be described as the following supplementary notes. However, the present invention is by no means limited thereto.

(Supplementary Note 1)
A cell treatment apparatus including:
 a cell treatment chamber in which cells in a cell culture vessel are treated;
 an observation unit that can observe the cells;
 a laser projection unit that can project a laser image onto the cells;
 a laser moving unit that can move the laser projection unit; and
 a control unit, wherein
 the laser projection unit includes:
 a laser light source; and
 a laser image generation portion that generates the laser image to be projected onto the cells from laser light oscillated from the laser light source,
 the control unit controls generation of the laser image by the laser image generation portion, and
 by moving the laser moving unit from a projection start position of the laser image at one end of the cell culture vessel to a projection end position of the laser image at the other end of the cell culture vessel, the laser projection unit projects the laser image from the projection start position of the laser image at one end of the cell culture vessel to the projection end position of the laser image at the other end of the cell culture vessel.

(Supplementary Note 2)
The cell treatment apparatus according to Supplementary Note 1, wherein
 the control unit stores laser image information associating laser position information, which is a position of the laser projection unit, with the laser image to be projected onto the cells at the position of the laser projection unit, acquires the laser position information, and controls the laser image generation portion to generate the laser image associated with the laser position information based on the laser position information and the laser image information.

(Supplementary Note 3)
The cell treatment apparatus according to Supplementary Note 1 or 2, wherein
 the laser projection unit moves from the projection start position to the projection end position at a substantially constant speed.

(Supplementary Note 4)
The cell treatment apparatus according to any one of Supplementary Notes 1 to 3, wherein
 the observation unit can image the cell, and
 the apparatus includes:
 an observation moving unit that can move the observation unit.

(Supplementary Note 5)
The cell treatment apparatus according to Supplementary Note 4, wherein
 the control unit acquires observation position information, which is a position of the observation unit, and the image obtained by the observation unit, and creates and stores the laser image information based on the observation position information and the image.

(Supplementary Note 6)
The cell treatment apparatus according to Supplementary Note 4 or 5, wherein
 the observation unit images an entire inside of the cell culture vessel, and
 the control unit creates the laser image based on an image of an entire cell culture vessel obtained, and creates and stores the laser image information associating the laser position information, which is the position of the laser projection unit, with the laser image to be projected onto the cells at the position of the laser projection unit.

(Supplementary Note 7)
The cell treatment apparatus according to any one of Supplementary Notes 4 to 6, wherein
 the observation unit images the cells in the entire cell culture vessel by dividing the cell culture vessel into a plurality of sections and imaging the plurality of sections.

(Supplementary Note 8)
The cell treatment apparatus according to Supplementary Note 7, wherein
 the control unit acquires an image of the entire cell culture vessel by integrating the images of the plurality of sections.

(Supplementary Note 9)
The cell treatment apparatus according to any one of Supplementary Notes 1 to 8, wherein
 the control unit divides the laser image into divided images having predetermined widths, and creates and then stores divided image information associating the laser position information, which is the position of the laser projection unit, with the divided image to be projected onto the cells at the position of the laser projection unit as the laser image information, and
 the laser projection unit projects the divided image as the laser image onto the cells.

(Supplementary Note 10)
The cell treatment apparatus according to any one of Supplementary Notes 4 to 9, wherein
 the observation unit images the entire inside of the cell culture vessel,
 the control unit creates the laser image based on the obtained image of the entire cell culture vessel, divides the laser image into divided images having predetermined widths, and creates and then stores the divided image information associating the laser position information, which is the position of the laser projection unit, with the divided image to be projected onto the cells at the position of the laser projection unit as the laser image information, and
 by moving the laser moving unit from a projection start position of the divided image at one end of the cell culture vessel to a projection end position of the divided image at the other end of the cell culture vessel, and then moving the laser moving unit from a projection start position of a new divided image at the other end of the cell culture vessel to a projection end position of the new divided image at one end of the cell culture vessel, the laser projection unit projects the divided image from the projection start position of the divided image at one end of the cell culture vessel to the projection end position of the divided image at the other end of the cell culture vessel, and the laser projection unit projects the divided image from the projection start position of the new divided image at the other end of the cell culture vessel to the projection end position of the divided image at one end of the cell culture vessel, whereby the laser moving unit and the laser projection unit move and project the divided image onto the cells in the entire cell culture vessel.

(Supplementary Note 11)
The cell treatment apparatus according to any one of Supplementary Notes 1 to 10, wherein
the laser image generation portion includes:
a spatial modulator.

(Supplementary Note 12)
The cell treatment apparatus according to Supplementary Note 11, wherein
the spatial modulator includes:
a digital micromirror device.

(Supplementary Note 13)
The cell treatment apparatus according to Supplementary Note 4, wherein
the laser moving unit and the observation moving unit are configured to be independently movable.

(Supplementary Note 14)
The cell treatment apparatus according to Supplementary Note 9 or 10, wherein
the divided image having a predetermined width is a band-shaped divided image having a predetermined width.

(Supplementary Note 15)
The cell treatment apparatus of any one of Supplementary Notes 1 to 14, wherein
the laser projection unit continuously projects the laser image from the projection start position of the laser image at one end of the cell culture vessel to the projection end position of the laser image at the other end of the cell culture vessel by continuously moving the laser projection unit to the projection end position of the laser image at the other end of the cell culture vessel.

(Supplementary Note 16)
A method for treating cells with lasers, the method including:
a treatment step of performing laser treatment by projecting a laser image onto cells in a cell culture vessel, wherein
in the treatment step, the laser treatment is performed by projecting the laser image from a projection start position of the laser image at one end of the cell culture vessel to a projection end position of the laser image at the other end of the cell culture vessel.

(Supplementary Note 17)
The method according to Supplementary Note 16, including:
a generation step of generating the laser image to be projected onto the cells based on an image containing the cells in the cell culture vessel.

(Supplementary Note 18)
The method according to Supplementary Note 17, including:
an acquisition step of acquiring the image containing the cells in the cell culture vessel.

(Supplementary Note 19)
The method according to Supplementary Note 18, wherein
in the acquisition step, the image is acquired by imaging the cells in the cell culture vessel.

(Supplementary Note 20)
The method according to Supplementary Note 18 or 19, wherein
in the acquisition step, an entire image containing cells is acquired on an entire cell culture vessel, and
in the generation step, the laser image to be projected onto the cells is generated based on the obtained entire image.

(Supplementary Note 21)
The method according to Supplementary Note 20, wherein
in the acquisition step, the cells in the entire cell culture vessel is imaged by dividing the cell culture vessel into a plurality of sections and imaging the plurality of sections.

(Supplementary Note 22)
The method according to Supplementary Note 21, wherein
in the acquisition step, an image of the entire cell culture vessel is acquired by integrating the obtained images of the plurality of sections.

(Supplementary Note 23)
The method according to any one of Supplementary Notes 16 to 22, including:
a dividing step of dividing the laser image into divided images having predetermined widths, wherein
in the treatment step, the laser treatment is performed by projecting the divided image as the laser image onto the cells in the cell culture vessel.

(Supplementary Note 24)
The method according to any one of Supplementary Notes 16 to 23, including:
a dividing step of dividing the laser image into divided images having predetermined widths, wherein
the treatment step includes:
a first treatment step of projecting the divided image from the projection start position of the divided image at one end of the cell culture vessel to the projection end position of the divided image at the other end of the cell culture vessel; and
a second treatment step of projecting the divided image from a projection start position of a new divided image at the other end of the cell culture vessel to a projection end position of the new divided image at one end of the cell culture vessel,
in the acquisition step, an entire image containing cells is acquired on an entire cell culture vessel,
in the generation step, the laser image to be projected onto the cells is generated based on the obtained entire image, and
in the treatment step, the first treatment step and the second treatment step are performed on the cells in the entire cell culture vessel.

(Supplementary Note 25)
The method according to any one of Supplementary Notes 16 to 24, wherein
the treatment step is performed using a laser projection apparatus,
the laser projection apparatus includes:
a laser light source; and
a laser image generation portion that generates a laser image to be projected onto the cells from laser light oscillated from the laser light source, and
in the treatment step, the laser treatment is performed by projecting the laser image generated by the laser image generation portion onto the cells.

(Supplementary Note 26)
The method according to Supplementary Note 25, wherein
the laser image generation portion includes:
a spatial modulator.

(Supplementary Note 27)
The method according to Supplementary Note 26, wherein
the spatial modulator includes:
a digital micromirror device.
(Supplementary Note 28)
The method according to any one of Supplementary Notes 25 to 27, wherein
the laser projection apparatus is a cell treatment apparatus according to any one of Supplementary Notes 1 to 15.
(Supplementary Note 29)
The method according to Supplementary Note 23 or 24, wherein
the divided image having a predetermined width is a band-shaped divided image having a predetermined width.
(Supplementary Note 30)
The method according to any one of claims 16 to 29, wherein
the laser image is continuously projected to the projection end position of the laser image at the other end of the cell culture vessel.

INDUSTRIAL APPLICABILITY

As described above, according to the cell treatment apparatus and the treatment method of the present invention, it is possible to suppress a variation of a treatment time of treating cells using laser light. Therefore, the present invention is considerably useful in, for example, the life sciences field, the pharmaceutical field, the regenerative medicine field, and the like in which cells, tissues, and the like are treated.

REFERENCE SIGNS LIST

1: cell treatment chamber
11: cell culture vessel
12: cell culture vessel placement unit
121: upper lid
122: bottom
123: translucent region
124: bottom wall
125: bottom plate
126: recess
127: projection
13, 13a, 13b: cell
2: observation unit
21, 21a, 21b, 21c: objective lens
3: observation moving unit
31: light source moving unit
31a, 32a: XY stage
31b, 32b: carriage
4: laser projection unit
41: laser light source
42: laser image generation portion
43: projection optical system
43a, 43b: lens
44: housing
45: opening
5: laser moving unit
51a, 51c: carriage
51b: XY stage
6: control unit
61: CPU
62: main memory
63: auxiliary storage device
64: video-codec
65: I/O interface
66: controller
211a, 211b: opening
212a, 212b: door
213: suction/discharge unit
214a: drainage container placement portion
214b: drainage container
214c: tip member detachment unit
215a: storage container placement portion
215b: storage container
216a: collection container
216b: collection container placement portion
217: camera
218a, 218b: illumination lamp
219: germicidal lamp
71: first chamber
72: second chamber
73: third chamber
24: circulator
24a: intake portion
24b: circulation path
24c: gas supply portion
24d: discharge portion
26: light source
27: power supply unit
100, 200: cell treatment apparatus

The invention claimed is:

1. A cell treatment apparatus comprising:
a cell treatment chamber in which cells in a cell culture vessel are treated;
an observation unit that images the cells;
a laser projection unit that projects a laser image onto the cells;
a laser moving drive unit that moves the laser projection unit; and
a controller, wherein
the laser projection unit comprises:
a laser emitter; and
a spatial modulator that generates a light of the laser image to be projected onto the cells from laser light oscillated from the laser emitter,
the controller is configured to control generation of the laser image by the laser image generation portion spatial modulator, and
by moving the laser moving drive unit from a projection start position of the laser image at one end of the cell culture vessel to a projection end position of the laser image at the other end of the cell culture vessel, the laser projection unit projects the light of the laser image from the projection start position of the laser image at one end of the cell culture vessel to the projection end position of the laser image at the other end of the cell culture vessel.

2. The cell treatment apparatus according to claim 1, wherein the controller is further configured to:
store laser image information associating laser position information, which is a position of the laser projection unit, with the laser image to be projected onto the cells at the position of the laser projection unit,
acquire the laser position information, and
control the spatial modulator to generate the light of the laser image associated with the laser position information based on the laser position information and the laser image information.

3. The cell treatment apparatus according to claim 1, wherein the laser projection unit moves from the projection start position to the projection end position at a substantially constant speed.

4. The cell treatment apparatus according to claim 1, wherein the apparatus comprises an observation moving drive unit that can moves the observation unit.

5. The cell treatment apparatus according to claim 4, wherein the controller is configured to:
   acquire observation position information, which is a position of the observation unit, and the image obtained by the observation unit; and
   create and store the laser image information based on the observation position information and the obtained image.

6. The cell treatment apparatus according to claim 4, wherein
   the observation unit images an entire inside of the cell culture vessel, and
   the controller is configured to:
      create the laser image based on an obtained image of an entire cell culture vessel; and
      create and store the laser image information associating the laser position information, which is the position of the laser projection unit, with the laser image to be projected onto the cells at the position of the laser projection unit.

7. The cell treatment apparatus according to claim 4, wherein the observation unit images the cells in the entire cell culture vessel by dividing the cell culture vessel into a plurality of sections and imaging the plurality of sections.

8. The cell treatment apparatus according to claim 7, wherein the controller is configured to acquire an image of the entire cell culture vessel by integrating the images of the plurality of sections.

9. The cell treatment apparatus according to claim 1, wherein
   the controller is configured to:
      divide the laser image into divided images having predetermined widths; and
      create and store divided image information associating the laser position information, which is the position of the laser projection unit, with the divided image to be projected onto the cells at the position of the laser projection unit as the laser image information, and
   the laser projection unit projects a light of the divided image as the laser image onto the cells.

10. The cell treatment apparatus according to claim 4, wherein
   the observation unit images the entire inside of the cell culture vessel,
   the controller is configured to:
      create the laser image based on the obtained image of the entire cell culture vessel,
      divide the laser image into divided images having predetermined widths, and
      create and store divided image information associating the laser position information, which is the position of the laser projection unit, with the divided image to be projected onto the cells at the position of the laser projection unit as the laser image information, and
   by moving the laser moving drive unit from a projection start position of the divided image at one end of the cell culture vessel to a projection end position of the divided image at the other end of the cell culture vessel, and then moving the laser moving drive unit from a projection start position of a new divided image at the other end of the cell culture vessel to a projection end position of the new divided image at one end of the cell culture vessel, the laser projection unit:
      projects the light of the divided image from the projection start position of the divided image at one end of the cell culture vessel to the projection end position of the divided image at the other end of the cell culture vessel, and
      projects the light of the divided image from the projection start position of the new divided image at the other end of the cell culture vessel to the projection end position of the divided image at one end of the cell culture vessel, wherein
         the laser moving drive unit and the laser projection unit move and project the light of the divided image onto the cells in the entire cell culture vessel.

11. The cell treatment apparatus according to claim 1, wherein the spatial modulator comprises a digital micromirror device.

12. The cell treatment apparatus according to claim 1, wherein
   the spatial modulator:
      generates the laser image to be projected onto the cells from laser light oscillated from the laser emitter, and
      projects the laser image generated by the light of the spatial modulator onto the cells;
   the controller is further configured to:
      acquire the laser image associated with the position of the laser projection unit, and
      control generation of the laser image associated with the position of the laser projection unit by the laser image generation portion, and
   by moving the laser moving unit continuously from a projection start position of the laser image at one end of the cell culture vessel to a projection end position of the laser image at the other end of the cell culture vessel, the laser projection unit continuously projects the light of the laser image associated with the position of the laser projection unit from the projection start position of the laser image at one end of the cell culture vessel to the projection end position of the laser image at the other end of the cell culture vessel.

* * * * *